United States Patent [19]

Fanshawe et al.

[11] 4,131,611

[45] Dec. 26, 1978

[54] AZABICYCLOHEXANES

[75] Inventors: William J. Fanshawe, Pearl River; Joseph W. Epstein, Monroe; Lantz S. Crawley, Spring Valley, all of N.Y.; Corris M. Hofmann, Ho-Ho-Kus; Sidney R. Safir, River Edge, both of N.J.

[73] Assignee: American Cyanamid Company, Stamford, Conn.

[21] Appl. No.: 809,339

[22] Filed: Jun. 23, 1977

Related U.S. Application Data

[63] Continuation-in-part of Ser. No. 723,402, Sep. 15, 1976, abandoned, which is a continuation-in-part of Ser. No. 601,128, Jul. 31, 1975, abandoned.

[51] Int. Cl.² .................... A01N 31/40; C07D 209/52

[52] U.S. Cl. ............................ 260/326.8; 260/326.32; 260/326.5 B; 260/326.85; 260/456 R; 260/456 P; 424/274; 560/76

[58] Field of Search ........................................ 260/326.8

[56] References Cited

U.S. PATENT DOCUMENTS 3,166,571  1/1965  Izzo et al. ...................... 260/326.5 B

OTHER PUBLICATIONS

Baltzly et al., Chem. Abstracts, vol. 56, cols. 14227–14229, (1962).

*Primary Examiner*—Alton D. Rollins
*Attorney, Agent, or Firm*—Claude J. Caroli

[57] ABSTRACT

Substituted 3-azabicyclo[3.1.0]hexanes, acid addition salts, method of use and method of preparation are described. The compounds have anxiolytic and analgesic activity.

69 Claims, No Drawings

AZABICYCLOHEXANES

This application is a continuation-in-part of our co-pending application Ser. No. 723,402, filed Sept. 15, 1976, now abandoned, which is in turn a continuation-in-part of our copending application Ser. No. 601,128, filed July 31, 1975, and now abandoned.

BACKGROUND OF THE INVENTION

Applicants are not aware of any prior art references which, in their respective judgment as one skilled in the anxiolytic and analgesic art, would anticipate or render obvious the novel compounds of the instant invention; however, for the purpose of fully developing the background of the invention and establishing the state of the requisite art, the following references are set forth: U.S. Pat. No. 3,166,571, U.S. Pat. No. 3,065,230, and *Synthesis of Pyrrolidines By Intramolecular Carbonionic Epoxide Opening*, R. Achini and W. Oppolzer, Tetrahedron Letters No. 6, 369–72 (1975).

SUMMARY OF THE INVENTION

The first embodiment of the instant invention is represented by optically active compounds of the formula:

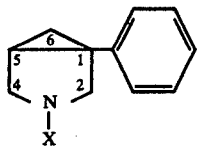

wherein the phenyl moiety is unsubstituted or mono- or di-substituted from the group consisting of halogen, straight chain $C_1$–$C_6$ alkyl, $C_1$–$C_6$ alkoxy, trifluoromethyl, nitro, amino, acetamido and hydroxy; X is selected from the group consisting of hydrogen, straight chain $C_1$–$C_8$ alkyl, and a moiety of the formula $C_nH_{2n}R_1$, wherein n is an integer from 1 to 3 and $R_1$ is selected from the group consisting of phenyl and p-fluorobenzoyl; the racemic mixture thereof; the mirror image thereof; and the non-toxic pharmaceutically acceptable salts thereof.

A preferred embodiment of the first embodiment consists of those compounds wherein the phenyl moiety is di-substituted from the group consisting of halogen, straight chain $C_1$–$C_6$ alkyl, $C_1$–$C_6$ alkoxy, trifluoromethyl, nitro, amino, acetamido and hydroxy; and X is as previously defined.

A second preferred embodiment of the first embodiment consists of those compounds wherein the phenyl moiety is unsubstituted or mono-substituted from the group consisting of halogen, straight chain $C_1$–$C_6$ alkyl, $C_1$–$C_6$ alkoxy, trifluoromethyl, nitro, amino, acetamido and hydroxy; and X is as previously defined.

A most preferred embodiment of the second preferred embodiment consists of those compounds wherein X is selected from the group consisting of hydrogen and straight chain $C_1$–$C_8$ alkyl.

A further preferred embodiment of the most preferred embodiment consists of those compounds wherein the phenyl moiety is para or meta substituted from the group consisting of straight chain $C_1$–$C_6$ alkyl, halogen and trifluoromethyl; and X is as previously defined.

A still further preferred embodiment of the further preferred embodiment consists of those compounds wherein the phenyl moiety is para or meta substituted from the group consisting of methyl, ethyl, chloro, fluoro, bromo and trifluoromethyl; and X is as previously defined.

A most preferred embodiment of the still further preferred embodiment consists of those compounds wherein the phenyl moiety is substituted as previously defined; and X is selected from the group consisting of hydrogen and methyl.

The second embodiment of the instant invention is represented by optically active compounds of the formula:

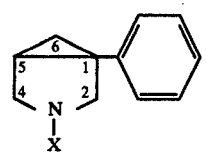

wherein the phenyl moiety is mono- or di-substituted from the group consisting of phenyl, halophenyl, $C_1$–$C_6$ alkoxy methyl and $C_3$–$C_6$ cycloalkyl; X is selected from the group consisting of hydrogen, straight chain $C_1$–$C_8$ alkyl, and a moiety of the formula $C_nH_{2n}R_1$, wherein n is an integer from 1 to 3 and $R_1$ is selected from the group consisting of halophenyl, bishalophenyl and aminophenyl; the racemic mixture thereof; the mirror image thereof; and the non-toxic pharmaceutically acceptable salts thereof.

A preferred embodiment of the second embodiment consists of those compounds wherein the phenyl moiety is di-substituted from the group consisting of phenyl, halophenyl, $C_1$–$C_6$ alkoxy methyl and $C_3$–$C_6$ cycloalkyl; and X is as previously defined.

A second preferred embodiment of the second embodiment consists of those compounds wherein the phenyl moiety is mono-substituted from the group consisting of phenyl, halophenyl, $C_1$–$C_6$ alkoxy methyl and $C_3$–$C_6$ cycloalkyl; and X is as previously defined.

A most preferred embodiment of the second preferred embodiment consists of those compounds wherein X is selected from the group consisting of hydrogen and straight chain $C_1$–$C_8$ alkyl.

A further preferred embodiment of the most preferred embodiment consists of those compounds wherein the phenyl moiety is para or meta substituted from the group consisting of phenyl, halophenyl, and $C_1$–$C_6$ alkoxymethyl; and X is as previously defined.

A still further preferred embodiment of the further preferred embodiment consists of those compounds wherein the phenyl moiety is para or meta substituted from the group consisting of phenyl, mono-chlorophenyl, di-chlorophenyl, methoxymethyl and ethoxymethyl; and X is as previously defined.

A most preferred embodiment of the still further preferred embodiment consists of those compounds wherein the phenyl moiety is substituted as previously defined; and X is selected from the group consisting of hydrogen and methyl.

The third embodiment of the instant invention is represented by optically active compounds of the formula:

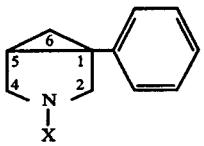

wherein the phenyl moiety is mono- or di-substituted from the group consisting of halogen, straight chain $C_1$–$C_6$ alkyl, $C_1$–$C_6$ alkoxy, trifluoromethyl, nitro, amino, acetamido and hydroxy; X is selected from the group consisting of $C_3$–$C_6$ cycloalkylmethyl, $C_3$–$C_6$ alkenyl and $C_3$–$C_6$ alkynyl; the racemic mixture thereof; the mirror image thereof; and the non-toxic pharmaceutically acceptable salts thereof.

A preferred embodiment of the third embodiment consists of those compounds wherein the phenyl moiety is di-substituted from the group consisting of halogen, straight chain $C_1$–$C_6$ alkyl, $C_1$–$C_6$ alkoxy, trifluoromethyl, nitro, amino, acetamido and hydroxy; and X is as previously defined.

A second preferred embodiment of the third embodiment consists of those compounds wherein the phenyl moiety is unsubstituted or mono-substituted from the group consisting of halogen, straight chain $C_1$–$C_6$ alkyl, $C_1$–$C_6$ alkoxy, trifluoromethyl, nitro, amino, acetamido and hydroxy; and X is as previously defined.

A most preferred embodiment of the second preferred embodiment consists of those compounds wherein X is selected from the group consisting of cyclopropylmethyl, cyclobutylmethyl, cyclopentylmethyl, allyl, butenyl, dimethylallyl and propargyl.

A further preferred embodiment of the most preferred embodiment consists of those compounds wherein the phenyl moiety is para or meta substituted from the group consisting of straight chain $C_1$–$C_6$ alkyl, halogen and trifluoromethyl; and X is as previously defined.

A still further preferred embodiment of the further preferred embodiment consists of those compounds wherein the phenyl moiety is para or meta substituted from the group consisting of methyl, ethyl, chloro, fluoro, bromo and trifluoromethyl; and X is as previously defined.

A most preferred embodiment of the further preferred embodiment consists of those compounds wherein the phenyl moiety is substituted as previously defined; and X is selected from the group consisting of cyclopropylmethyl, allyl and propargyl.

The fourth embodiment of the instant invention is represented by optically active compounds of the formula:

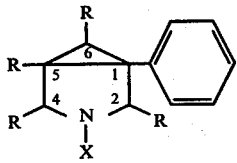

wherein the phenyl moiety is unsubstituted or mono- or di-substituted from the group consisting of halogen, straight chain $C_1$–$C_6$ alkyl, $C_1$–$C_6$ alkoxy, trifluoromethyl, nitro, amino, acetamido and hydroxy; X is selected from the group consisting of hydrogen, straight chain $C_1$–$C_8$ alkyl, $C_3$–$C_6$ cycloalkylmethyl, $C_3$–$C_6$ alkenyl, $C_3$–$C_6$ alkynyl, and a moiety of the formula $C_nH_{2n}R_1$, wherein n is an integer from 1 to 3 and $R_1$ is selected from the group consisting of phenyl and p-fluorobenzoyl; R is selected from the group consisting of hydrogen and $C_1$–$C_3$ alkyl; with the proviso that at least one R must be selected from the group consisting of $C_1$–$C_3$ alkyl; the racemic mixture thereof; the mirror image thereof; and the non-toxic pharmaceutically acceptable salts thereof.

A preferred embodiment of the fourth embodiment consists of those compounds wherein the phenyl moiety is di-substituted from the group consisting of halogen, straight chain $C_1$–$C_6$ alkyl, $C_1$–$C_6$ alkoxy, trifluoromethyl, nitro, amino, acetamido and hydroxy; and R and X are as previously defined.

A second preferred embodiment of the fourth embodiment consists of those compounds wherein the phenyl moiety is unsubstituted or mono-substituted from the group consisting of halogen, straight chain $C_1$–$C_6$ alkyl, $C_1$–$C_6$ alkoxy, trifluoromethyl, nitro, amino, acetamido and hydroxy; and R and X are as previously defined.

A most preferred embodiment of the second preferred embodiment consists of those compounds wherein X is selected from the group consisting of hydrogen and straight chain $C_1$–$C_8$ alkyl; and R is as previously defined.

A further preferred embodiment of the most preferred embodiment consists of those compounds wherein the phenyl moiety is para or meta substituted from the group consisting of straight chain $C_1$–$C_6$ alkyl, halogen and trifluoromethyl; and R and X are as previously defined.

A still further preferred embodiment of the further preferred embodiment consists of those compounds wherein the phenyl moiety is para or meta substituted from the group consisting of methyl, ethyl, chloro, fluoro, bromo and trifluoromethyl; X is as previously defined; and R is mono-substituted at the carbon 2- or carbon 4-position.

A most preferred embodiment of the still further preferred embodiment consists of those compounds wherein the phenyl moiety is substituted as previously defined; X is selected from the group consisting of hydrogen and methyl; and R is as previously defined.

The fifth embodiment of the instant invention is represented by optically active compounds of the formula:

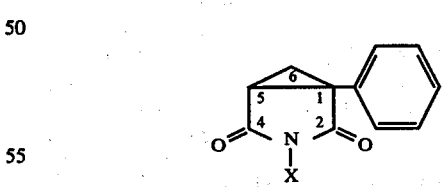

wherein the phenyl moiety is mono-substituted from the group consisting of $C_1$–$C_6$ alkyl; and X is selected from the group consisting of hydrogen and $C_1$–$C_8$ alkyl.

A preferred embodiment of the fifth embodiment consists of those compounds wherein the phenyl moiety is mono-substituted from the group consisting of $C_1$–$C_3$ alkyl; and X is selected from the group consisting of hydrogen and $C_1$–$C_3$ alkyl.

A most preferred embodiment of the preferred embodiment consists of those compounds wherein the phenyl moiety is mono-substituted at the para-position with a compound selected from the group consisting of methyl and ethyl; and X is selected from the group consisting of hydrogen and methyl.

The sixth embodiment of the instant invention is represented by optically active compounds of the formula:

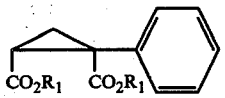

wherein the phenyl moiety is mono-substituted from the group consisting of $C_1$–$C_6$ alkyl; and $R_1$ is selected from the group consisting of hydrogen and $C_1$–$C_6$ alkyl.

A preferred embodiment of the sixth embodiment consists of those compounds wherein the phenyl moiety is mono-substituted from the group consisting of $C_1$–$C_3$ alkyl; and X is selected from the group consisting of hydrogen and $C_1$–$C_3$ alkyl.

A most preferred embodiment of the preferred embodiment consists of those compounds wherein the phenyl moiety is mono-substituted at the para-position with a compound selected from the group consisting of methyl and ethyl; and X is selected from the group consisting of methyl and ethyl; and X is selected from the group consisting of hydrogen and methyl.

The seventh embodiment of the instant invention is represented by optically active compounds of the formula:

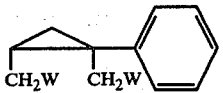

wherein the phenyl moiety is mono-substituted from the group consisting of halogen, straight chain $C_1$–$C_6$ alkyl, $C_1$–$C_6$ alkoxy, trifluoromethyl, nitro, amino, acetamido and hydroxy; and W is selected from the group consisting of electronegative leaving moieties.

A preferred embodiment of the seventh embodiment consists of those compounds wherein the phenyl moiety is mono-substituted as previously defined; and W is selected from the group consisting of methanesulfonyl, toluenesulfonyl, chloride, iodine and bromine.

A most preferred embodiment of the preferred embodiment consists of those compounds wherein the phenyl moiety is mono-substituted at the para-position from the group consisting of methyl, ethyl, chloro, fluoro, bromo and trifluoromethyl; and X is methanesulfonyl.

The salts can be, for example, hydrochloride, hydrobromide, hydriodide, sulfate, nitrate, phosphate, maleate, succinate and the like.

DESCRIPTION OF THE INVENTION

The compounds of the present invention may be prepared by the following reaction sequence:

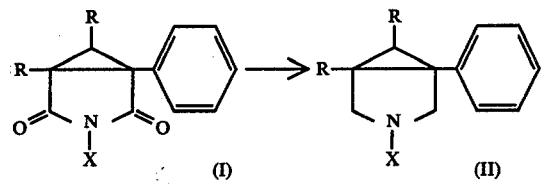

wherein R and X are as defined above; the compounds of Formula I are dissolved in a solvent such as benzene, toluene, ether, tetrahydrofuran, and, the like and reacted with a reducing agent such as sodium bis(2-methoxyethoxy)aluminum hydride at a temperature from about 0° to 125° C., preferably from 25° C. to about 80° C., for a period of 1 to 4 hours. The reaction mixture is cooled and a strong base such as potassium hydroxide is added. The organic layer is concentrated and the product is collected by filtration.

The starting material shown as compounds (I) above may be prepared as follows:

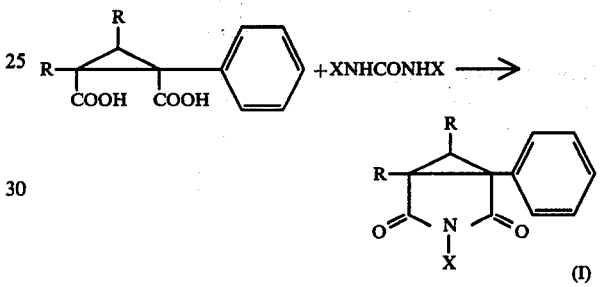

wherein R and X are as defined above.

The reaction ingredients are heated in an aprotic solvent, such as xylene, for 6–24 hours and the product is recovered by evaporation of the solvent.

In producing the compounds of formula (II) a wide variety of other hydride reducing agents, such as, diborane or lithium aluminum hydride may be used. In this instance the compounds of formula (I) are suspended in tetrahydrofuran, the reducing agent is added and the reaction is carried out at 0°–80° C. for 1 to 4 hours. The reaction mixture is cooled, acidified with an acid such as hydrochloric, the aqueous layer is separated and the product is liberated by the addition of a strong base such as potassium hydroxide.

Alternatively, the compounds of this invention of formula II above may be prepared by the reaction of lactams of either of the following formulae:

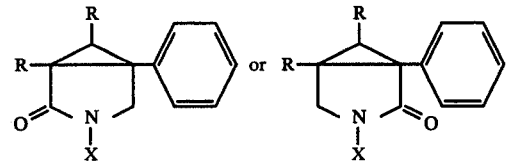

wherein R and X are as defined above, with a suitable reducing agent, such as lithium aluminum hydride, diborane, sodium bis(2-methoxyethoxy)aluminum hydride in an aprotic solvent such as ether, benzene, or tetrahydrofuran at a temperature of 0°–80° C. for a period of 1 to 6 hours. The compound of formula II is isolated as described above for the reduction of the corresponding imides of formula I.

The above reduction may be carried out with a limited quantity of the above mentioned reducing agents so that when R is as defined above and X is hydrogen the intermediates of the following formulae may also be obtained:

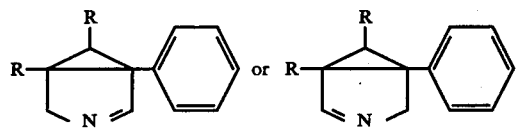

and when R and X are as defined above, with the proviso that X is not hydrogen, intermediates of the following formulae may be obtained:

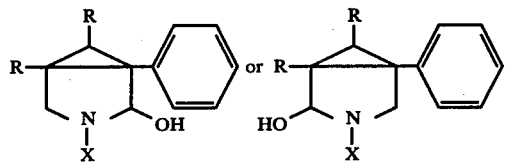

These compounds may then be reduced to the compounds of this invention of formula II, by the methods as described above.

Alternatively, the compounds of formula (II) may be prepared, using the same conditions, from compounds of the following formula:

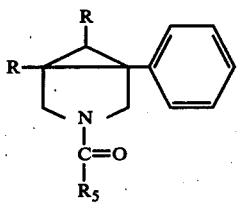

wherein R is as defined above and $R_5$ is selected from the group consisting of $C_1-C_6$ alkyl, hydrogen, $C_3-C_6$ cycloalkyl, and phenyl.

The compounds of formula II, above, may also be prepared by the cyclization of a compound of the formula:

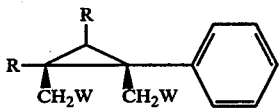

(III)

wherein R is as defined above, and W is a suitable leaving group such as bromide, chloride, iodide, methanesulfonyloxy or p-toluenesulfonyloxy groups, with sodamide, wherein R is hydrogen, or with a compound of the formula $XNH_2$ wherein X is as defined above, in a solvent such as ethanol or methanol, at a temperature of from about 0° to about 150° C. An acid binding agent such as sodium carbonate, ethyldiisopropylamine and the like are usually employed.

Compounds of formula III may be prepared by the reaction of diols of the formula:

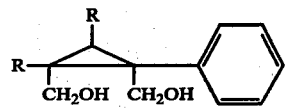

wherein R is as defined above, with phosphorous pentabromide, hydrogen bromide, hydrogen iodide, hydrogen chloride-zinc chloride, thionyl chloride, phosphorous pentachloride, methanesulfonyl chloride, or p-toluenesulfonyl chloride.

The above diols may be prepared from compounds of the formula:

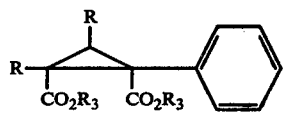

wherein R is as defined above and $R_3$ is selected from the group consisting of hydrogen and $C_1-C_6$ alkyl, by reaction with diborane, lithium aluminum hydride or sodium bis(2-methoxyethoxy)aluminum hydride in an aprotic solvent such as ether, benzene or tetrahydrofuran at a temperature of from about 0° to about 80° C. for a period of from about 1 to about 6 hours. The reaction mixture is cooled and the product is liberated by hydrolysis of the reaction product using acids or bases in a manner known to those skilled in the art.

These cyclopropane-1,2-dicarboxylic esters are also useful intermediates in other procedures for the compounds of this invention. For example, when saponified to the cyclopropane-1,2-dicarboxylic acids they are useful for the cyclopropane-1,2-dicarboximides (I), as described above; and the cyclopropane-1,2-dicarboxylic acids are also useful in resolution procedures (as described below).

The diesters above, wherein $R_3$ is $C_1-C_6$ alkyl, may be prepared by reaction of a bromoester of the formula:

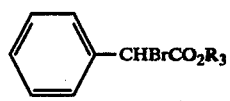

wherein $R_3$ is as described above, with an acrylic ester of the formula:

RCH=CRCOOR₃ wherein R and $R_3$ are as described above, using a suitable base such as lithium hydride, sodium hydride, sodium methoxide, or potassium tert-butoxide in a suitable aprotic solvent such as ether, benzene, or tetrahydrofuran, as described in U.S. Pat. No. 3,344,026. The desired cis-isomers are the predominant products of this reaction.

Certain cis-diacids of the formula:

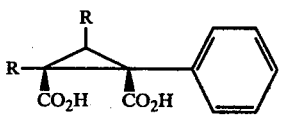

wherein R is as described above may be prepared by heating the following compounds with a suitable base such as sodium hydroxide or potassium hydroxide in a suitable solvent such as methanol, ethanol or water at a temperature of from about 30° to about 100° C., from about 3 to about 18 hours, followed by liberation of the free diacid with a suitable mineral acid such as hydrochloric acid or sulfuric acid:

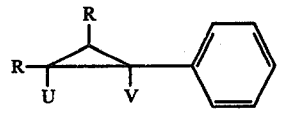

wherein R is as defined above and U and V are the same or different and are selected from the group consisting of —CO$_2$R$_4$, where R$_4$ is selected from the group consisting of C$_1$-C$_6$ alkyl, and cyano.

Compounds of the previous structure wherein U is cyano and V is —CO$_2$R$_3$ may be prepared by the reaction of a bromoester of the formula:

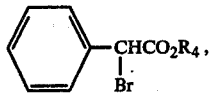

wherein R$_4$ is as described above, and an acrylonitrile of the formula RHC=CRCN, in a manner as described above for the preparation of the diesters. Compounds of the previous structure wherein U is —CO$_2$R$_4$ and V is cyano may be prepared by the reaction of a bromophenylacetonitrile of the formula:

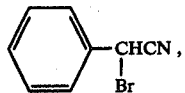

with an acrylic ester is described above.

A lactam of the formula:

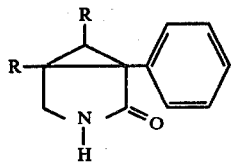

wherein R is as defined above may be prepared from the above described cyanoesters of the formula:

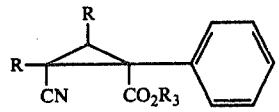

wherein R and R$_3$ are as described above by reduction with diborane in a solvent such as tetrahydrofuran, at from about 0° to about 60° C. for about 1 to about 3 hours, followed by reaction of the intermediate reduction product with a mineral acid such as 6N hydrochloric acid. Similarly, a lactam of the formula:

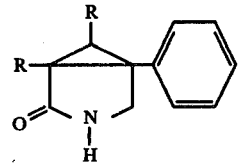

wherein R is as defined above, may be prepared from a cyanoester of the formula:

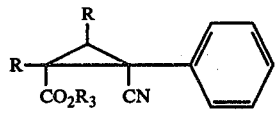

wherein R and R$_3$ are as described above, by reduction in a manner as previously described.

By another alternative route, a compound of formula (II) of this invention wherein R is hydrogen may be prepared by the reaction of 3-phenyl-3-pyrroline of the formula:

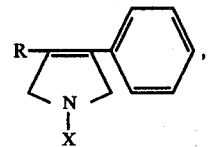

wherein R and X are as described above, with a compound of the formula CH$_2$I$_2$ under the conditions of the Simmons-Smith reaction as described by N. Kawabuton, et al., J. Amer. Chem. Soc., 98, 2676 (1976).

Additionally, new compounds of the present invention of the formula:

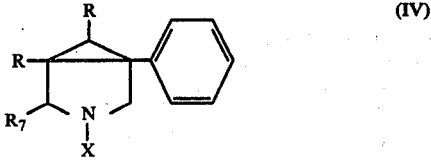

(IV)

wherein R and X are as defined above, and R$_7$ is selected from the group consisting of C$_1$-C$_3$ alkyl, with the proviso that the phenyl moiety may not be substituted with hydroxy, acetamido or amino, may be prepared from a lactam of the formula:

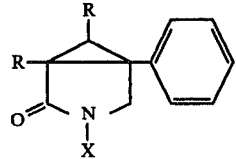

wherein R and X are as described above, by reaction with a organometallic compound such as methyl lithium, followed by reaction of the intermediate enamine with sodium borohydride [M. Takeda, et al., Chem. Pharm. Bull., 24, 2312 (1976)].

In a like manner a compound of the formula:

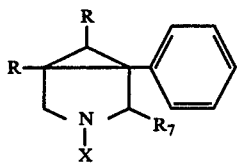

wherein R, $R_7$, and X are as described previously, may be prepared from a compound of the formula:

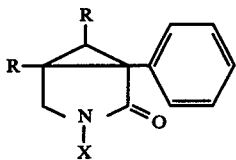

wherein R and X are as described above.

The above lactams, wherein X is other than hydrogen, and is as described above, may be prepared from the corresponding lactams wherein X is hydrogen by alkylation of the union of the lactam as described above for the alkylation of the corresponding imides.

Alternatively, a compound of formula (I) above may be reacted with a Grignard reagent, R'Mg Halogen, such as methylmagnesium iodide, or ethylmagnesium bromide in an aprotic solvent such as ether, benzene or tetrahydrofuran, at from about 0° to about 25° C., for about 1 to about 18 hours, followed by hydrolysis of the reaction product with water to give a hydroxylactam of the formula:

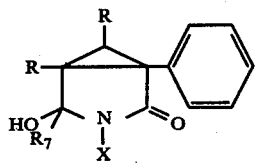

wherein R, $R_7$ and X are as defined above. The above hydroxylactam may be reduced to a compound of this invention of the formula (IV) in the general manner described above.

Amides of the formula:

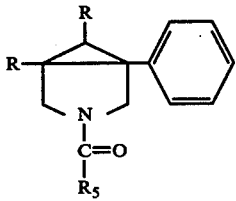

may be prepared from compounds of formula (II), above, wherein R is hydrogen, by reaction with acid halides of the formula $R_5COX$, where X is chlorine, bromine or the imidazolyl group, or with anhydrides of the formula $(R_5CO)_2O$, wherein $R_5$ is as defined above, in a suitable solvent such as pyridine, water or benzene, and using an acid binding agent such as sodium hydroxide, triethylamine, or sodium carbonate, at from about 0° to about 80° C., for about 30 minutes to about 18 hours.

Alternatively, new compounds of the present invention of formula (II), wherein R is other than hydrogen, as described above, may be prepared from a compound of formula (II) where R is hydrogen, by an alkylation reaction with a compound of the formula $R_5CH_2W$ where $R_5$ is as defined above, or a p-fluorobenzoylethyl group, or 4,4-bis(p-fluorophenyl)propyl group in a solvent such as methanol, ethanol, or ether, using an acid binding agent such as sodium carbonate, at from about 25° to about 80° C. for about 1 to about 18 hours.

Alternatively, an imide of formula (I) wherein R is hydrogen may be alkylated with a compound of the formula $R_5CH_2W$ as described above, by reaction of the imide with a strong, non-nucleophilic base such as sodium hydroxide or potassium tert-butoxide in a solvent such as N,N-dimethylformamide, followed by combination with the alkylating agent. The alkylating agent may also be a compound of the formula $R_5CHWR_6$ where $R_5$ and W are as described above, and $R_6$ is selected from the group consisting of $C_1$-$C_6$ alkyl.

The novel compounds of this invention exist as optical isomers which comprise racemic dextrorotatory and levorotatory forms. This invention contemplates all such isomeric forms. The optical isomers of the compounds of this invention may be prepared by a variety of resolution procedures.

By one method, a cis-diacid of the formula:

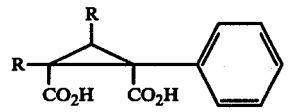

wherein R is as defined above, may be combined with an optically active amine such as (−)-α-(1-naphthyl)ethylamine in a suitable solvent such as methanol, ethanol, acetone, tetrahydrofuran, or acetonitrile to give a salt comprised of one molecular equivalent of the (+)-diacid and one molecular equivalent of the above (−)-amine. In some cases, and particularly when the phenyl moiety is substituted with one or more alkyl groups, and specifically where the aryl moiety is the p-tolyl group and both R are hydrogen, it is advantageous to use a tetrahydrofuran-ether mixture as the solvent.

The above racemic diacid can also be combined with (−)-2-amino-1-butanol in a suitable solvent, as previously described, to give a salt wherein the acid moiety is the (+)-diacid. The above salts can be converted to the corresponding (+)-diacid by combination of the above salts with a suitable base such as sodium hydroxide, potassium hydroxide, ammonium hydroxide or potassium carbonate followed by acidification of the aqueous solution with a suitable acid such as hydrochloric acid or sulfuric acid. For the (−)-diacid, a cis-diacid of the formula:

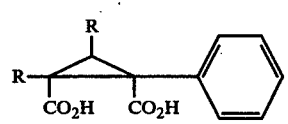

wherein R is as described above, may be combined with an optically active amine such as brucine, or (+)-α-(1-naphthyl)ethylamine or (+)-2-amino-1-butanol in a suitable solvent, as described above, to give salts wherein the acid moiety is the (−)-diacid.

These salts can be converted to the corresponding (−)-diacid in the manner described above. The (+) or (−) diacids described above may be converted to the compounds:

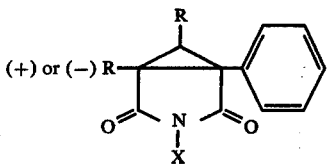

wherein R and X are as defined above, by the methods described above. These imides may be reduced by the methods described above to give the optically active forms of the compounds of this invention:

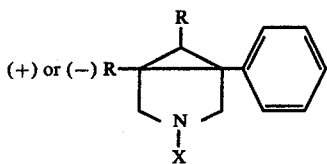

wherein R and X are as defined above.

Alternatively, a racemic compound of the formula:

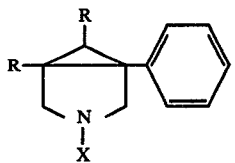

wherein R and X are as defined above, may be combined with an optically active acid such as (+) or (−)-mandelic acid, (+) or (−)-tartanic acid, (+) or (−)-di-O-benzoyltartanic acid or (+) or (−)-di-O-(p-toluoyl)-tartanic acid in a suitable solvent such as methanol, ethanol, acetone, acetonitrile, or tetrahydrofuran to give a salt. Combination of the above salt with a suitable acid such as hydrochloric acid or sulfuric acid, with subsequent basification of the aqueous solution with a base such as sodium hydroxide, potassium hydroxide, ammonium hydroxide or sodium carbonate, gives the compound of this invention:

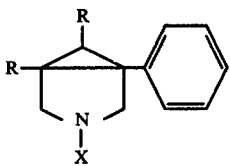

wherein R and X are as defined above, in an optically active form.

Among the azabicyclohexanes included within the scope of this invention are:
1-(p-Chlorophenyl)-3-azabicyclo[3.1.0]hexane
1-Phenyl-3-azabicyclo[3.1.0]hexane
3-Methyl-1-phenyl-3-azabicyclo[3.1.0]hexane
1-(m-Chlorophenyl)-3-azabicyclo[3.1.0]hexane
1-(m-Fluorophenyl)-3-azabicyclo[3.1.0]hexane
1-(p-Chlorophenyl)-3-methyl-3-azabicyclo[3.1.0]hexane
3-Benzyl-1-phenyl-3-azabicyclo[3.1.0]hexane
3-Cyclopropylmethyl-1-phenyl-3-azabicyclo[3.1.0]hexane
3-Phenethyl-1-phenyl-3-azabicyclo[3.1.0]hexane
3-Isopropyl-1-phenyl-3-azabicyclo[3.1.0]hexane
1-(p-Trifluoromethylphenyl)-3-azabicyclo[3.1.0]hexane
3-(p-Chlorobenzyl)-1-(p-chlorophenyl)-3-azabicyclo[3.1.0]hexane
3-Allyl-1-phenyl-3-azabicyclo[3.1.0]hexane
3-Ethyl-1-phenyl-3-azabicyclo[3.1.0]hexane
3-Cyclohexylmethyl-1-phenyl-3-azabicyclo[3.1.0]hexane
1-(p-Methoxyphenyl)-3-azabicyclo[3.1.0]hexane
1-(p-Chlorophenyl)-3-(o-fluorobenzyl)-3-azabicyclo[3.1.0]hexane
1-Phenyl-5-methyl-3-azabicyclo[3.1.0]hexane
3-Methyl-1-(3,4,5-trimethoxyphenyl)-3-azabicyclo[3.1.0]hexane
1-(p-Tolyl-3,6-dimethyl-3-azabicyclo[3.1.0]hexane
3-(2-Naphthylmethyl)-1-(p-chlorophenyl)-3-azabicyclo[3.1.0]hexane
3-(5-Norbornen-2-ylmethyl)-1-(p-chlorophenyl)-3-azabicyclo[3.1.0]hexane
3-Ethyl-1-(p-aminophenyl)-3-azabicyclo[3.1.0]hexane
1-(p-Chlorophenyl)-3-propargyl-3-azabicyclo[3.1.0]hexane
3-(p-Fluorobenzoyl)-1-phenyl-3-azabicyclo[3.1.0]hexane
3-(m-Fluorobenzoyl)-1-phenyl-3-azabicyclo[3.1.0]hexane
3,4-Dichlorophenyl-3-azabicyclo[3.1.0]hexane
1-(m-Methoxyphenyl)-3-methyl-3-azabicyclo[3.1.0]hexane
(+)-Phenyl-3-methyl-3-azabicyclo[3.1.0]hexane
1-(4-Chloro-α,α,α-trifluoro-m-tolyl)-3-azabicyclo[3.1.0]hexane
3,6-Dimethyl-1-phenyl-3-azabicyclo[3.1.0]hexane
1-(p-Acetamidophenyl)-3-ethyl-3-azabicyclo[3.1.0]hexane
1-(m-Hydroxyphenyl)-3-methyl-3-azabicyclo[3.1.0]hexane
1-(p-Nitrophenyl)-3-azabicyclo[3.1.0]hexane
1-(p-tolyl)-3-azabicyclo[3.1.0]hexane hydrochloride
1-(o-Chlorophenyl)-3-azabicyclo[3.1.0]hexane The compounds of the present invention are useful as analgesic agents in warm-blooded animals, as evident from testing by several procedures. One method is a modification of the method of Randall and Selitto [Arch. Int. Pharmacodyn., 111, 409 (1957)]. This test measures the pain threshold of rats whose paws are made sensitive to pressure by the injection of 0.1 ml of a 20% aqueous suspension of brewers' yeast into the plantar surface of the left hind paw. Constantly increasing force (16 g/second) is applied to the swollen paw using an Analgesey Meter, Ugo Basile. The pressure is cut off at 250 g of force if there is no response (sudden struggle or vocalization). Control rats treated with starch vehicle respond to a pressure of about 30 g. Pressure-pain thresholds are recorded one to several hours after administration of the test compound (at the estimated time of peak effect) at doses up to 200 mg/kg orally. The brewers' yeast is administered two hours before measurement of the pain threshold. Ratios of treated (T)/control (C) are calculated, and are used to determine screening activity, to estimate potency by means of dose response experiments, and/or to measure analgesic efficacy (i.e. the higher the T/C ratio the greater the analgesic efficacy). For example, test compounds may be considered as active (significant over parallel controls) when they produce a 100% elevation of the pain threshold (T/C ≧ 2.0). An active screening result may be followed up by one or more of the following experiments: repeat testing at the same dose for confirmation; testing at a lower dose; determination of duration and time of peak effect; dose-response estimates of potency; determination of the efficacy ceiling (maximum T/C), using experimental protocols well known to those skilled in the art.

Representative compounds of the present invention also exhibit analgesic activity when measured by a modification of the method of D. C. Atkinson and A. Cowan, J. Pharm. pharmacol. 26, 727 (1974).

In this test male, albino Wistar strain rats from Royalhart farms, weighing 120–150 g are deprived of food for about 20 hours. A 40% suspension of brewers' yeast in physiological saline is injected, at a concentration of 0.25 ml/rat into the plantar surface of the left hind paw of each rat. Three hours later, at which time an inflammation of the injected paw has developed, a pre-drug assessment of walking gait is made for each rat according to the following scoring system:

0 = Normal giat in the presence of a severely inflammed paw. There is continuous use of the foot pad.
0.5 = As above with intermittent mild limping.
1.0 = Constant limping, but continuous use of the foot pad.
1.5 = Limping with occasional three-legged gait (paw kept off walking surface) or intermittent use of digits in combination with foot pad.
2.0 = Continuous three-legged gait and/or only the tips of the digits touch the walking surface. There is no use of the foot pad.

More than 95% of the rats exhibit a gait score of 2 before given a test compound. Compounds, in a suitable vehicle, are administered orally by gavage in a volume of 0.5 ml/100 g of body weight. One and/or two hours later a post-drug assessment of walking gait is made as described above. The post-treatment score is then measured and compared with the pretreatment score. These results are used for determination of screening activity, for dose response estimates of potency, etc. For example, when screening experiments are carried out using 3 animals per dose, the pretreatment score is 6(2.0 × 3) and a post-treatment score of 4 (for 3 animals) may be considered as significant activity over parallel controls. For dose-response estimates, an individual animal may be considered to show an analgesic effect when there is a ≧ 50% reversal of the abnormal gait score (≦ 1.0 post-drug) from the pre-drug score (2.0).

Another method for measuring the activity of the compounds of the present invention is the "writhing syndrome" test for analgesic activity as described by Siegmund, et al., Proc. Soc. Exp. Biol. and Med., 95, 729 (1957), with modifications. This method is based upon the reduction of the number of writhes following the intraperitoneal injection of one mg/kg of body weight of phenyl-p-quinone in male Swiss albino mice weighing 18–25 gm. The syndrome is characterized by intermittent contractions of the abdomen, twisting and turning of the trunk, and extension of the hind legs beginning 3 to 5 minutes after injection of the phenyl-p-quinone. The test compounds are administered orally at the indicated dose to groups of 2 mice each, 30 minutes before injection of the phenyl-p-quinone. The total number of writhes exhibited by each group of mice is recorded for a 3 minute period commencing 15 minutes after injection of the phenyl-p-quinone. A compound is considered active if it reduces the total number of writhes in 2 test mice from a control value of approximately 30 per pair to a value of 18 or less.

When representative compounds of the present invention are tested by one or more of the above described analgesic procedures the results are summarized in the following Tables (I and II):

TABLE 1
Analgesic Screening

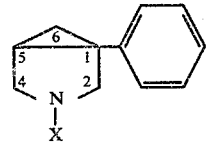

| Phenyl Substituent | X | Reversal of Abnormal Gait (Rat) | Antiwrithing (Mouse) | Inflamed Paw-Pain (Rat) |
|---|---|---|---|---|
| p-Cl | H | A(100)* | A(50)* | A(100)* |
| p-Cl | H (−)-Isomer |  | A(100) |  |
| p-Cl | H (+)-Isomer | A(50) | A(100) | A(50) |
| H | H | A(150) | A(100) | A(200) |
| H | Me | A(150) | A(100) | A(200) |
| m-Cl | H | A(50) | A(200) | A(50) |
| m-F | H |  | A(100) | A(50) |
| H | H (−)-Isomer |  | A(100) | A(50) |
| H | Me (−)-Isomer |  | A(50) |  |
| p-Cl | Me (−)-Isomer |  | A(100) |  |
| p-Cl | Me (+)-Isomer | A(150) | A(100) |  |
| p-Cl | Me |  | A(100) |  |
| H | —CH2—⟨phenyl⟩ | A(200) |  |  |
| H | —CH2CH2—⟨phenyl⟩ |  | A(100) |  |
| p-CF3 | H | A(150) |  | A(50) |
| H | Et | A(200) |  |  |
| p-MeO | H | A(100) |  | A(50) |
| H | H (+)-Isomer | A(200) | A(50) | A(50) |

TABLE 1-continued
Analgesic Screening

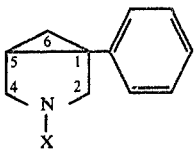

| | | Procedure | | |
|---|---|---|---|---|
| Phenyl Substituent | X | Reversal of Abnormal Gait (Rat) | Antiwrithing (Mouse) | Inflamed Paw-Pain (Rat) |
| 3,4-Di-Cl | H | A(200) | | |
| p-Et | H | A(25) | | A(50) |
| m-Me | H | A(50) | A(25) | A(50) |
| p-Br | H | A(200) | | |
| p-F | H | A(100) | A(50) | A(50) |
| p-Br | H | A(200) | | |
| | —CH₂—⟨phenyl⟩ | | | |
| m-MeO | Me | A(100) | A(50) | A(50) |
| H | Me (+)-Isomer | A(200) | | |
| 4-Cl-3-CF₃ | H | A(200) | | |
| p-NO₂ | H | A(200) | | |
| p-Me | H | A(200) | A(60) | A(50) |
| m-CF₃ | H | A(25) | | A(50) |
| 3-Br-4-MeO | H | A(200) | | |
| p-Me | H (+)-Isomer | A(50) | A(25) | A(50) |
| p-Me | H (−)-Isomer | | A(100) | A(50) |
| p-Me | Me | A(100) | | A(50) |
| p-OH | H | A(200) | | A(50) |
| p-EtO | H | A(50) | | |
| p-Cl | Et | | A(100) | |
| H | | A(200) | | |
| | —(CH₂)₃CH⟨(4-F-phenyl)(4-F-phenyl)⟩ | | | |
| p-Cl | | A(200) | | |
| | —(CH₂)₃CH⟨(4-F-phenyl)(4-F-phenyl)⟩ | | | |
| H | | A(200) | | |
| | —(CH₂)₃CO—(4-F-phenyl) | | | |
| m-MeO | H | A(200) | | |

*Active (at indicated dose, mg/kg orally).

TABLE 2

Median Effective Doses:

Reversal of abnormal gait in the rat:
 ED₅₀ calculated as the 50% level for animals showing an analgesic effect defined at ≧ 50% reversal of the abnormal gait score [absorption time (minutes) in parentheses].

Antiwrithing in the mouse:
 ED₅₀ calculated as the 50% level for groups of 2 mice showing an analgesic effect defined as ≦ 18 writhes per pair.

Inflamed paw-pain in the rat:
 ED₅₀ calculated as the 50% level for animals showing an analgesic effect defined as T/C ≧ 2.0 [absorption time (minutes) in parentheses].

| | Procedure |
|---|---|
| | Reversal of |

TABLE 2-continued

| Phenyl Substituent | X | Abnormal Gait (Rat) | Antiwrithing (Mouse) | Inflamed Paw-Pain (Rat) |
|---|---|---|---|---|
| p-Cl | H | ~50(120') | 21 | ~12.5(120') |
| p-Cl | H (−)-Isomer |  | <100 |  |
| p-Cl | H (+)-Isomer | 25(120') | 18.5 | <12.5(120') |
| H | H | 70(90') | <100 | >50(120') |
| m-Cl | H | >50(120') | 34 | >50(120') |
| m-F | H |  | 21 | >50(120') |
| H | H (−)-Isomer |  | <50 | ~50(120') |
| p-CF$_3$ | H | 38(90') |  | ~50(120') |
| p-MeO | H | 24(90') | 4.4 | 42(60') |
| H | H (+)-Isomer | ~200(120') |  | >50(120') |
| p-Et | H | 13(90') |  | ~50(120') |
| m-Me | H | >50(120') | 17.5 | ~25(120') |
| p-F | H | >50(120') | 34 | 13.5(120') |
| p-Me | H | 14.3(60')po | 13.2 | 9.2(60')po |
|  |  | 4.2(60')sc |  | 10.1(120')sc |
| m-CF$_3$ | H | ~25(120') |  | ~50(120') |
| p-Me | H (+)-Isomer | 8.9(60') | 16 | ~12.5(120') |
| p-Me | H (−)-Isomer |  | ~100 | >50(120') |
| p-Me | Me | 20(90') |  | ~25(120') |

*ED$_{50}$, mg/kg orally (po), unless otherwise noted (at absorption time, in minutes): sc = subcutaneous administration.

Certain compounds of this invention also show anti-anxiety activity by their ability to protect warm-blooded animals from convulsions resulting from the administration of pentylenetetrazole. Dose levels of the test compounds are administered orally in a 2% starch vehicle to groups of at least 4 rats. At the estimated time of peak effect, the rats are treated intravenously with pentylenetetrazole at a dose of 21 to 23 mg/kd of body weight. This dose is estimated to cause clonic seizures in 99% of unprotected rats. Protection (or lack, thereof) against these seizures is measured in each animal. When a test compound is screened in a group of 4 rats, protection in 2, 3 or 4 animals is considered significant activity over parallel controls (>25% protection). In follow-up tests the effective dose of the test compounds for protection of 50% of the animals (ED$_{50}$) may be calculated by the method of D. H. Finney in *Statistical Methods in Biological Assay*, Second Edition, Hofner Publishing Co., New York pp. 456–457, (1964) or by the method of J. T. Litchfield and J. Wilcoxon, Pharmacol. and Exp. Ther., 96, 99 (1949). It has been reported [R. T. Hill and D. H. Tedeschi, "Animal Testing and Screening Procedures in Evaluating Psychotropic Drugs", in An Introduction to Psychopharmacology, Eds. R. R. Rech and K. E. Moore, Raven Press, New York, pp 237–288 (1971)] that there is a high degree of correlation between anti-convulsant effects in rodents and anti-anxiety effects in higher warm-blooded animals. The results of this test on representative compounds of the present invention appear in Table III.

TABLE 3

| Compound | Median Effective Dose (mg/kg) oral |
|---|---|
| 1-(p-Chlorophenyl)-3-azabicyclo-[3.1.0]hexane hydrochloride | 15 |
| (-)-1-(p-Chlorophenyl)-3-azabicyclo-[3.1.0]hexane hydrochloride | 24 |
| 1-Phenyl-3-azabicyclo[3.1.0]hexane hydrochloride | 103 |
| 1-(p-Fluorophenyl)-3-azabicyclo-[3.1.0]hexane hydrochloride | 15 |
| 3-Cyclopropylmethyl-1-phenyl-3-azabicyclo[3.1.0]hexane hydrochloride | Active (50) |

The azabicyclohexanes of the present invention can be orally administered, for example, with an inert diluent or with an assimilable edible carrier, or they may be enclosed in hard or soft shell gelatin capsules, or they may be compressed into tablets, or they may be incorporated directly with the food or the diet. For oral therapeutic administration, the active compounds of this invention may be incorporated with excipients and used in the form of tablets, troches, capsules, elixirs, suspensions, syrups, wafers, and the like. Such compositions and preparations should contain at least 0.1% of active compound. The percentage in the compositions and preparations may, of cours, be varied and may conveniently be between about 5% to about 75% or more of the weight of the unit. The amount of active compound in such therapeutically useful compositions or preparations is such that a suitable dosage will be obtained. Preferred compositions or preparations according to the present invention are prepared so that an oral dosage unit form contains between 10 and 400 milligrams of active compound. A most preferred composition would be an oral dosage unit form containing from about 50 to 250 milligrams of active compound.

The tablets, troches, pills, capsules and the like may also contain the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; and a sweetening agent such as sucrose, lactose, or saccharin may be added or a flavoring agent such as peppermint, oil of wintergreen, or cherry flavoring. When the dosage unit form is a capsule, it may contain in addition to materials of the above type a liquid carrier such as a fatty oil. Various other materials may be present as coatings or to otherwise modify the physical form of the dosage unit, for instance, tablets, pills or capsules may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially non-toxic in the amounts employed.

Compositions having the desired clarity, stability, and adaptability for parental use are obtained by dissolving from 0.10% to 10.0% by weight of the azabicyclohexane in a vehicle consisting of a mixture of nonvolatile, normally liquid polyethylene glycols which are soluble in both water and organic liquids and which have molecular weights of from about 200 to about 1500. Such mixtures of polyethylene glycols are commercially available and are usually obtained by condensing glycol with ethylene oxide. Although the amount of azabicyclohexane dissolved in the above vehicle may vary from 0.10% to 10.0% by weight, it is preferred that the amount employed be from about 3.0% to about 9.0% by weight. Although various mixtures of the aforementioned nonvolatile polyethylene glycols may be employed, it is preferred to use a mixture of non-volatile polyethylene glycols having an average molecular weight of about 400. Such a mixture is usually referred to as polyethylene glycol 400. A preferred embodiment comprises a clear solution of from about 3.0% to about 9.0% by weight of the azabicyclohexane dissolved in an aqueous solution of polyethylene glycol 400. In addition to the azabicyclohexane, the parenteral solutions may also contain various preservatives which may be used to prevent bacterial and fungal contamination or chemical degradation.

SPECIFIC EXAMPLES

The following specific examples describe in detail the preparation of representative compounds of this invention.

DETAILED DESCRIPTION OF THE INVENTION

EXAMPLE 1

Preparation of Racemic
1-(p-Chlorophenyl)-3-azabicyclo[3.1.0]hexane
hydrochloride A solution of 2 g of diethyl 1-(p--chlorophenyl)-cis-1,2-cyclopropanedicarboxylate (U.S. Pat. No. 3,344,026, Ex. 1) in 25 ml of ethanol is treated with 13.5 ml of 1N potassium hydroxide solution. The reaction mixture is refluxed for 3.5 hours and then is allowed to stand at room temperature overnight. The ethanol is removed under reduced pressure and the aqueous solution is extracted with ether to remove a small amount of mineral oil. The aqueous solution is treated with 13.5 ml of 1N hydrochloric acid and 2 ml of 6N hydrochloric acid. The oily aqueous mixture is extracted four times with chloroform. The chloroform solution is dried, decolorized, and concentrated under reduced pressure to give a yellow solid. Two recrystallizations from ethyl acetate-petroleum ether (30°-70° C.) gives 0.85 g of a white solid, 1-(p-chlorophenyl)-cis-1,2-cyclopropanedicarboxylic acid, m.p. 162°-163° C.

A 5.7 g portion of the above acid and 2.02 g of urea in 200 ml of xylene is refluxed for 22 hours, cooled, diluted with benzene and washed with water. The organic layer is diluted with chloroform, dried, concentrated under reduced pressure and recrystallized from ethyl acetate and petroleum ether to give 1-(p-chlorophenyl)-1,2-cyclopropanedicarboximide.

To a stirred solution f 30 ml of sodium bis(2-methoxyethoxy)aluminum hydride (70% benzene solution) is added dropwise a solution of 2.2 g of 1-(p-chlorophenyl)-1,2-cyclopropanedicarboximide in 100 ml of benzene over a 30 minute period at room temperature under nitrogen atmosphere. The reaction vessel is warmed slightly to maintain solution. The clear yellow solution is then heated to reflux under nitrogen atmosphere for one hour. The solution is cooled and the excess reagent decomposed with 5N sodium hydroxide. Water is added to the mixture and the benzene phase is separated. The aqueous phase is extracted with ether and the ether extracts are combined with the benzene phase and dried over magnesium sulfate. This organic phase is evaporated under reduced pressure to give a viscous liquid, which crystallizes to a tacky off-white solid consisting of the racemic base 1-(p-chlorophenyl)-3-azabicyclo[3.1.0]hexane. This solid is dissolved in ethanol, acidified with ethanolic hydrogen chloride, and ether is added producing off-white crystals of the hydrochloride. This is recrystallized from ethanol giving off-white crystals, mp 215°-217° C.

In a like manner, reductions of the following imides with sodium bis-(2-methoxyethoxy)aluminum hydride yield the corresponding reduced products.

| Imide | Reduction Product |
|---|---|
| 1-phenyl-2-methyl-1,2-cyclopropanedicarboximide (U.S. 3,166,571-Example 15) | 1-phenyl-5-methyl-3-azabicyclo-[3.1.0]hexane hydrochloride, m.p. 161°-163° C. |
| N-methyl-1-(3,4,5-tri-methyoxyphenyl)-1,2-cyclopropanedicarboximide (U.S. 3,166,571-Example 4) | 3-methyl-1-(3,4,5-trimethyoxyphenyl)-3-azabicyclo[3.1.0]-hexane hydrochloride, m.p. 243°-245° C. |
| 1-(p-tolyl)-3,N-dimethyl-1,2-cyclopropanedicarboximide (U.S. 3,166,571-Example 11) | 1-(p-tolyl)-3,6-dimethyl-3-azabicyclo[3.1.0]hexane |

EXAMPLE 2

Preparation of
(−)-1-(p-Chlorophenyl)-3-azabicyclo[3.1.0]hexane
hydrochloride

To a stirred solution of 30 ml of sodium bis(2-methoxyethoxy)aluminum hydride (70% benzene solution) is added dropwise a solution of 6.6 g of (−)-1-(p-chlorophenyl)-1,2-cyclopropanedicarboximide (U.S. Pat. No. 3,892,772) in 500 ml. of benzene over a 3 hour period at room temperature under nitrogen. The clear yellow solution is heated at reflux for 90 minutes under nitrogen and then stored overnight at room temperature. The excess hydride reagent is decomposed by the cautious addition of 25 ml of 5N sodium hydroxide. The mixture is then diluted with 200 ml of water. The benzene phase is separated and the aqueous phase is extracted with chloroform. The combined benzene and chloroform phases are dried over magnesium sulfate and concentrated under reduced pressure to give (−)-1-(p-chlorophenyl)-3-azabicyclo[3.1.0]hexane as a yellow solid. This solid is dissolved in ethanol and acidified with 10 ml of 2.3N ethanolic hydrogen chloride. The addition of ether causes the precipitation of the hydrochloride of this base as a solid which is collected and dried giving white crystals, m.p. 197°-200° C. $[\alpha]_D^{CH_3OH} = -67°$.

EXAMPLE 3

Preparation of
(+)-1-(p-chlorophenyl)-3-azabicyclo[3.1.0]hexane
hydrochloride

A 192.5 g portion of racemic cis-1-(p-chlorophenyl)1,2-cyclopropanedicarboxylic acid (U.S. Pat. No. 3,892,772) and 142 g of (−)-2-aminobutanol in 1600 ml of acetone is allowed to stand for 48 hours, filtered and washed with acetone giving a solid. This solid is dissolved in 460 ml of warm water and acidified. The solid is filtered and air dried. A 107.5 g portion of this crude (+)-diacid and 79.3 g of (−)-2-aminobutanol in 892 ml of acetone are allowed to stand several hours. The solid is filtered, dried, dissolved in 200 ml of warm water, acidified with concentrated hydrochloric acid, cooled and filtered. This solid is recrystallized from acetonitrile giving (+)-cis-1-(p-chlorophenyl)-1,2-cyclopropanedicarboxylic acid, $[\alpha]_D^{CH_3OH} = +180°$.

A 10.5 g portion of this (+)-diacid and 3.9 g of urea in 325 ml of xylene is stirred and then refluxed for 7½ hours and then allowed to stand overnight. Distilling off the xylene, cooling and filtration produces a white solid which is recrystallized from ethanol giving (+)-1-(p-chlorophenyl)-1,2-cyclopropanedicarboximide $[\alpha]_D^{CH_3OH} = +63°$.

To a stirred solution of 30 ml of sodium bis(2-methoxyethoxy)aluminum hydride (70% benzene solution) is added dropwise a solution of 4.5 g of (+)-1-(p-chlorophenyl)-1,2-cyclopropanedicarboximide in 400 ml of benzene during a 45 minute period with stirring at room temperature under nitrogen. The clear yellow solution is heated at reflux under nitrogen for 90 minutes and stored overnight at room temperature. The excess hydride reagent is decomposed by the cautious addition of 25 ml of 5N sodium hydroxide. The mixture is diluted with 200 ml of water and the benzene phase is removed. The aqueous phase is extracted with chloroform. The combined benzene and chloroform phases are dried over magnesium sulfate and concentrated under reduced pressure to give (+)-1-(p-chlorophenyl)-3-azabicyclo[3.1.0]hexane as a tacky yellow solid. This solid is dissolved in ethanol and acidified with 20 ml of 2.3N ethanolic hydrogen chloride. A 200 ml volume of ether is added and crystals form. These are recrystallized from acetonitrile to give the hydrochloride as white crystals, m.p. 190°–192° C.; $[\alpha]_D^{CH_3OH} = +63°$ C.

EXAMPLE 4

Preparation of Racemic
1-Phenyl-3-azabicyclo[3.1.0]hexane hydrochloride

To a stirred solution of 30 ml of sodium bis(2-methoxyethoxy)aluminum hydride (70% benzene solution) is added dropwise a solution of 6.6 g of 1-phenyl-1,2-cyclopropanedicarboximide (U.S. Pat. No. 3,166,571-Ex. 8) in 400 ml of benzene, during one hour at room temperature under nitrogen. The reaction mixture is then heated at reflux under nitrogen for 90 minutes. The excess hydride reagent is decomposed by the cautious addition of 25 ml of 10N sodium hydroxide. The mixture is diluted with 200 ml of water and the benzene phase is separated. The aqueous phase is extracted with chloroform and the combined organic extracts are dried over magnesium sulfate. The solution is concentrated under reduced pressure to give a brown liquid which is dissolved in ethanol and acidified with 5 ml of 2.3N ethanolic hydrogen chloride. The addition of ether precipitates a solid which is recrystallized from acetonitrile to give white crystals, mp 166°–168° C.

EXAMPLE 5

Preparation of Racemic
3-Methyl-1-phenyl-3-azabicyclo[3.1.0]hexane hydrochloride To a stirred solution of 30 ml of sodium bis(2-methoxyethoxy)aluminum hydride (70% benzene solution) is added dropwise a solution of 5.5 g of N-methyl-1-phenyl-1,2-cyclopropanedicarboximide (U.S. Pat. No. 3,166,571-Ex. 1) in 400 ml of benzene over a one hour period at room temperature under nitrogen. The mixture is heated at reflux under nitrogen for 90 minutes. The excess hydride reagent is decomposed by the cautious addition of 25 ml of 10N sodium hydroxide and then diluted to 200 ml with water. The benzene phase is separated and the aqueous phase is extracted with chloroform. The combined organic phases are dried over magnesium sulfate and concentrated under reduced pressure giving a liquid. The liquid is dissolved in ethanol and acidified with 15 ml of 2.3 N ethanolic hydrogen chloride. The addition of ether causes the formation of a solid which is recrystallized from isopropyl alcohol-hexane giving white crystals, m.p. 158°–160° C.

EXAMPLE 6

Preparation of
1-(m-Chlorophenyl)-3-azabicyclo[3.1.0]hexane hydrochloride

A 53.6 g portion of ethyl m-chlorophenylacetate (prepared by esterification of the corresponding acid), 51.5 g of N-bromosuccinimide and one gram of benzoyl peroxide in 1.25 liters of carbon tetrachloride is stirred with a Nichrome metal stirrer and refluxed for 20 hours. The mixture is cooled, filtered and concentrated to an orange oil. Vacuum distillation yields the product ethyl α-bromo-m-chlorophenylacetate.

To a stirred suspension of 4.4 g of sodium hydride in 500 ml of ether under nitrogen is added 0.5 ml of ethanol. A mixture of 27.8 g of the above ester, 10 g of ethyl acrylate and one ml of ethanol is added dropwise and the mixture is stirred at room temperature overnight. Ethanol is added to decompose the unreacted sodium hydride and the mixture is washed with 100 ml of water, 50 ml of 1N hydrochloric acid, three times with dilute sodium bicarbonate and finally with 100 ml of water. The product is dried and concentrated under reduced pressure to a yellow liquid, 1-(m-chlorophenyl)-1,2-cyclopropanedicarboxylic acid diethyl ester.

A 22 g portion of this diester in 150 ml of ethanol and 150 ml of 1N potassium hydroxide is refluxed for 3.5 hours and then allowed to stand at room temperature overnight. The mixture is concentrated and extracted with ether. The aqueous phase is acidified with 1N hydrochloric acid, extracted three times with chloroform, dried and concentrated under reduced pressure to a yellow oil which is crystallized from ethyl acetate-petroleum ether to give cis-1-(m-chlorophenyl)-1,2-cyclopropanedicarboxylic acid as a white solid.

A 5.7 g portion of this acid and 2.02 g of urea in 200 ml of xylene is refluxed for 22 hours, cooled, diluted with benzene and washed with water. The organic layer is diluted with chloroform, dried, concentrated under reduced pressure, and recrystallized from ethyl acetate and petroleum ether to give 1-(m-chlorophenyl)-1,2-cyclopropanedicarboximide.

To a stirred solution of 30 ml of sodium bis(2-methoxyethoxy)aluminum hydride (70% benzene solution) is added dropwise a solution of 4.0 g of 1-(m-chlorophenyl)-1,2-cyclopropanedicarboximide in 400 ml of benzene during 1 hour at room temperature under nitrogen. The reaction is heated at reflux under nitrogen for 90 minutes. The excess hydride reagent is decomposed with 25 ml of 10N sodium hydroxide and the mixture is diluted with 200 ml of water. The benzene phase is removed and the aqueous phase is extracted with chloroform. The combined organic phases are dried over magnesium sulfate and concentrated under reduced pressure to give a viscous orange-brown liquid. This liquid is dissolved in ethanol and acidified with 2.3N ethanolic hydrogen chloride. The addition of ether precipitates a solid which is recrystallized from isopropanol to give 1-(m-chlorophenyl)-3-azabicyclo[3.1.0-

]hexane hydrochloride as white crystals, mp 182°–184° C.

EXAMPLE 7

Preparation of 1-(m-Fluorophenyl)-3-azabicyclo[3.1.0]hexane hydrochloride

A 46.2 g portion of 1-(m-fluorophenyl)acetic acid is dissolved in 120 ml of ethanol. A 12 ml portion of sulfuric acid is added, the mixture is refluxed for 4.5 hours and then allowed to stand at room temperature overnight. A 400 ml portion of water is added and the mixture is extracted three times with ether, dried over magnesium sulfate and concentrated under reduced pressure to a liquid. Vacuum distillation produces ethyl 1-(m-fluorophenyl)-acetate.

A mixture of 49.3 g of ethyl 1-(m-fluorophenyl)acetate, 53 g of N-bromosuccinimide and 0.95 g of benzoyl peroxide in 1.6 liters of carbon tetrachloride is refluxed and stirred with a Nichrome metal stirrer for 24 hours, concentrated to an orange oil and vacuum distilled giving ethyl α-bromo-1-(m-fluorophenyl)acetate.

To a suspension of 11 g of sodium hydride in mineral oil in one liter of ether under nitrogen is added dropwise, with stirring a mixture of 65 g of ethyl α-bromo-1-(m-fluorophenyl)acetate, 25 g of ethyl acrylate and 2 ml of ethanol. The temperature is maintained at 25°–29° C. with stirring overnight. The mixture is cooled, a few ml of ethanol is added to decompose the unreacted sodium hydride and the mixture is washed successively with water, 1N hydrochloric acid, dilute sodium bicarbonate and saturated sodium chloride solution, then concentrated to a liquid which is vacuum distilled giving the diethyl ester of 1-(m-fluorophenyl)-1,2-cyclopropanedicarboxylic acid.

A mixture of 20.5 g of the above diester and 160 ml of 1N potassium hydroxide in 150 ml of ethanol is refluxed for 3.5 hours and concentrated. The mixture is acidified with 1N hydrochloric acid, extracted three times with chloroform, dried and concentrated under reduced pressure to a solid. The solid is recrystallized twice from ethyl acetate-petroleum ether giving cis-1-(m-fluorophenyl)-1,2-cyclopropanedicarboxylic acid.

A stirred mixture of 8.0 g of the above diacid and 2.6 g of urea in 500 ml of xylene is heated under reflux for 22 hours. The solution is diluted with benzene, washed with water and dried over magnesium sulfate. The organic layer is concentrated under reduced pressure to give 1-(m-fluorophenyl)-1,2-cyclopropanedicarboximide as an off-white solid.

To a stirred solution of 30 ml of sodium bis(2-methoxyethoxy)aluminum hydride is added dropwise a solution of 5.6 g of 1-(m-fluorophenyl)-1,2-cyclopropanedicarboximide in 400 ml of benzene during 90 minutes, under nitrogen at room temperature. The reaction mixture is heated at reflux, under nitrogen for 90 minutes. The excess hydride reagent is decomposed by the cautious addition of 25 ml of 10N sodium hydroxide and then the mixture is diluted with 200 ml of water. The benzene phase is removed and the aqueous phase is extracted with chloroform. The combined organic solutions are dried over magnesium sulfate and concentrated under reduced pressure to give a mixture of an oily solid and a viscous liquid. This mixture is dissolved in ethanol and acidified with ethanolic hydrogen chloride. The addition of ether gives a precipitate which is recrystallized from acetonitrile to give 1-(m-fluorophenyl)-3-azabicyclo[3.1.0]hexane hydrochloride as gray crystals, mp 140°–146° C.

EXAMPLE 8

Preparation of (−)-1-Phenyl-3-azabicyclo[3.1.0]hexane hydrochloride

To a stirred slurry of 18.7 g of (−)-1-phenyl-1,2-cyclopropanedicarboximide in 500 ml of benzene under nitrogen is added 150 ml of sodium bis(2-methoxyethoxy)aluminum hydride (70% benzene solution) over a period of 10 minutes. The mixture is stirred at room temperature for 2 hours, refluxed for 4 hours and then allowed to stand at room temperature for 20 hours. A 150 ml portion of 10N sodium hydroxide is added cautiously with stirring. The organic layer is washed with water, dried over magnesium sulfate and evaporated under reduced pressure to a yellow oil. This oil is dissolved in 300 ml of ether. Dry hydrogen chloride gas is bubbled through until precipitation ceases and the mixture is filtered giving colorless crystals. These are recrystallized from acetonitrile giving pale tan crystals, mp 170°–172° C.

EXAMPLE 9

Preparation of Racemic 1-Phenyl-3-azabicyclo[3.1.0]hexane

Employing 1-phenyl-1,2-cyclopropanedicarboximide (U.S. Pat. No. 3,166,571-Ex. 8) in the procedure of Example 8 without the addition of hydrogen chloride gas there is produced racemix 1-phenyl-3-azabicyclo[3.1.0]hexane, bp 130°–133° C. (15 mm).

EXAMPLE 10

Preparation of (−)-3-Methyl-1-phenyl-3-azabicyclo[3.1.0]hexane hydrochloride To a solution of 18.7 g of (−)-1-phenyl-1,2-cyclopropanedicarboximide in 100 ml of anhydrous dimethylformamide is added 5.0 g of sodium hydride (54% in mineral oil) over 15 minutes. The mixture is stirred for 30 minutes and then 10 ml of iodomethane is added over 5 minutes. The mixture is allowed to stand for 15 minutes, heated on a steam bath for 15 minutes, cooled and poured into 250 ml of water. The mixture is filtered and the crystals are washed with petroleum ether and air dried giving (−)-N-methyl-1-phenyl-1,2-cyclopropanedicarboximide.

To a stirred solution of 5.0 g of (−)-N-methyl-1-pehnyl-1,2-cyclopropanedicarboximide in 125 ml of benzene under nitrogen is added 30 ml of sodium bis(2-methoxyethoxy)aluminum hydride (70% benzene solution) over 10 minutes. The mixture is refluxed for 5 hours, cooled and 60 ml of 10N sodium hydroxide is added cautiously. The organic layer is washed with water, dried over magnesium sulfate and evaporated under reduced pressure to give an amber oil. This oil is dissolved in 250 ml of ether, saturated with hydrogen chloride and filtered giving colorless crystals. These crystals are recrystallized from acetonitrile giving colorless crystals, mp 194°–196° C. $[\alpha]_D^{CH_3OH} = -73°$.

EXAMPLE 11

Preparation of
(−)-1-(p-Chlorophenyl)-3-methyl-3-azabicyclo[3.1.0-]hexane hydrochloride To a solution of 22.1 g of (−)-1-(p-chlorophenyl)-1,2-cyclopropanedicarboximide in 100 ml of anhydrous dimethylformamide is added 5.0 g of sodium hydride (54% in mineral oil) over a 15 minute period. The mixture is stirred for 30 minutes and then 10 ml of iodomethane is added over 5 minutes. This mixture is allowed to stand 15 minutes, heated on a steam bath 15 minutes, cooled and poured into 250 ml of water. The crystals are filtered, washed with petroleum ether and air dried giving colorless crystals of (−)-N-methyl-1-(p-chlorophenyl)-1,2-cyclopropanedicarboximide.

To a stirred solution of 11.8 g of the above product in 250 ml of benzene under nitrogen is added 60 ml of sodium bis(2-methoxyethoxy)aluminum hydride (70% benzene solution) over 10 minutes. The mixture is refluxed for 5 hours, cooled and 60 ml of 10N sodium hydroxide is added cautiously. The organic layer is washed with water, dried over magnesium sulfate and evaporated under reduced pressure to an amber oil. The oil is dissolved in 250 ml of ether, saturated with hydrogen chloride and filtered to give colorless crystals. Recrystallization from acetonitrile gives colorless crystals, mp 211°–212° C., $[\alpha]_D^{CH_3OH} = -68°$.

EXAMPLE 12

Preparation of
(+)-1-(p-Chlorophenyl)-3-methyl-3-azabicyclo[3.1.0-]hexane hydrochloride To a stirred solution of 11.08 g of (+)-1-(p-chlorophenyl)-1,2-cyclopropanedicarboximide in 50 ml of anhydrous dimethylformamide is added 2.5 g of sodium hydride (54% in mineral oil) over 15 minutes under nitrogen. The mixture is stirred for 30 minutes and 5 ml of iodomethane is added over 5 minutes. The mixture is allowed to stand 15 minutes, is heated on a steam bath 15 minutes, cooled and poured into 125 ml of water. The mixture is filtered, washed with petroleum ether and dried giving colorless crystals of (+)-N-methyl-(1-(p-chlorophenyl)-1,2-cyclopropanedicarboximide.

To a stirred solution of 3.92 g of (+)-N-methyl-1-(p-chlorophenyl)-1,2-cyclopropanedicarboximide in 100 ml of benzene, under nitrogen, is added 20 ml of sodium bis(2-methoxyethoxy)aluminum hydride (70% benzene solution), during 10 minutes. The mixture is stirred for 2 hours at room temperature and then refluxed for 2 hours. A 20 ml portion of 10N sodium hydroxide is added cautiously. The benzene layer is washed with water, dried over magnesium sulfate and evaporated under reduced pressure giving an oil. The oil is dissolved in 200 ml of ether and saturated with dry hydrogen chloride giving a colorless crystalline cake which is recrystallized from acetonitrile to give (+)-1-(p-chlorophenyl)-3-methyl-3-azabicyclo[3.1.0]hexane hydrochloride as pale tan crystals, mp 209°–210° C., $[\alpha]_D^{CH_3OH} = +67°$.

EXAMPLE 13

Preparation of Racemic
1-(p-Chlorophenyl)-3-methyl-3-azabicyclo[3.1.0]hexane hydrochloride To a stirred solution of 44.2 g of racemic 1-(p-chlorophenyl)-1,2-cyclopropanedicarboximide in 200 ml of anhydrous dimethylformamide is added 10.0 g of sodium hydride (50% in mineral oil) over a 5 minute period. A 20 ml portion of iodomethane is added slowly with stirring over 5 minutes. The mixture is then heated on a steam bath for 30 minutes, cooled and poured into 500 ml of water. The solid is collected by filtration and recrystallized from heptane-ethyl acetate giving colorless crystals of racemic N-methyl-1-(p-chlorophenyl)-1,2-cyclopropanedicarboximide.

To a stirred solution of 11.8 g of the above product in 250 ml of benzene, under nitrogen, is added 60 ml of sodium bis(2-methoxyethoxy)aluminum hydride (70% benzene solution) over 10 minutes. After standing for 16 hours the mixture is refluxed for 4 hours, cooled and 60 ml of 10N sodium hydroxide is cautiously added. The organic layer is dried over sodium sulfate, then magnesium sulfate, filtered and evaporated under reduced pressure to give the free base as a pale yellow oil. The oil is dissolved in 200 ml of ether and saturated with dry hydrogen chloride gas. The solid is recovered and crystallized from acetonitrile giving pale tan plates, mp 180°–182° C.

EXAMPLE 14

Preparation of
3-Benzyl-1-phenyl-3-azabicyclo[3.1.0]hexane hydrochloride

To 37.4 g of 1-phenyl-1,2-cyclopropanedicarboximide in 200 ml of anhydrous dimethylformamide is added 10 g of sodium hydride (50% in mineral oil) with stirring. A 25.4 ml portion of benzyl chloride is added dropwise. A 20 mg portion of potassium iodide is added. The mixture is stirred at room temperature for 2 hours and then poured into one liter of water producing a gummy residue which is treated with petroleum ether to produce N-benzyl-1-phenyl-1,2-cyclopropanedicarboximide as pale yellow crystals.

To a stirred solution of 13.87 g of the above product in 250 ml of benzene, under nitrogen, is added 60 ml of sodium bis(2-methoxyethoxy)aluminum hydride (70% benzene solution) over a period of 10 minutes. The mixture is refluxed for 5 hours, cooled and 60 ml of 10N sodium hydroxide is added cautiously. The benzene layer is washed with water, dried over magnesium sulfate and evaporated under reduced pressure to an amber oil. The oil is dissolved in ether, dry hydrogen chloride gas is added and the solid is recovered and recrystallized from isopropyl alcohol giving colorless crystals, mp 194°–196° C.

EXAMPLE 15

Preparation of
3-Cyclopropylmethyl-1-phenyl-3-azabicyclo[3.1.0]hexane hydrochloride To a stirred slurry of 61.2 g of 1-phenyl-1,2-cyclopropanedicarboximide (U.S. Pat. No. 3,166,571-Example VIII) in 2 liters of benzene is added 400 ml of sodium bis(2-methoxyethoxy)aluminum hydride 70% solution in benzene under nitrogen. The mixture is stirred at room temperature for 2 hours, refluxed for 4 hours and then stirred at room temperature for 20 hours. A 400 ml portion of 10N sodium hydroxide is added cautiously with stirring. The organic layer is washed twice with dilute sodium hydroxide and then with water, dried over magnesium sulfate and evaporated to give an amber oil. This oil is dissolved in dilute hydrochloric acid, washed with ether, filtered and the filtrate made basic with sodium hydroxide. The basic filtrate is extracted with benzene, dried over magnesium sulfate, filtered and evaporated to give 1-phenyl-3-azabicyclo[3.1.0]hexane as an amber oil. To a solution of 15.9 g of 1-phenyl-3-azabicyclo[3.1.0]hexane in 100 ml of benzene and 20 ml of triethylamine is added 11.0 g of cyclopropanecarboxylic acid chloride in 20 ml of benzene over 5 minutes. The mixture is stirred for 30 minutes and 50 ml of water is added. The benzene layer is extracted with dilute sodium bicarbonate followed by dilute hydrochloric acid and then water, dried over magnesium sulfate and evaporated to give the product 3-cyclopropylcarbonyl-1-phenyl-3-azabicyclo[3.1.0]hexane as a brown oil.

To a solution of 11.35 g of 3-cyclopropylcarbonyl-1-phenyl-3-azabicyclo[3.1.0]hexane (prepared above) in 100 ml of benzene is added 25 ml of sodium bis(2-methoxyethoxy)aluminum hydride (70% benzene solution) with stirring. The mixture is allowed to stand for 18 hours, is refluxed for 2 hours, cooled and 25 ml of 10N sodium hydroxide is slowly added. The organic layer is washed with saturated sodium chloride, dried over magnesium sulfate and evaporated to a brown oil. This oil is dissolved in ether and dry hydrogen chloride gas is bubbled in producing pink crystals. These crystals are recrystallized from isopropyl alcohol giving pink crystals, mp 164°–165° C.

In a like manner 1-(p-tolyl)-3-azabicyclo[3.1.0]hexane (Example 36) is reacted with cyclopropanecarbonyl chloride to give 3-cyclopropanecarbonyl-1-(p-tolyl)-3-azabicyclo[3.1.0]hexane which is reduced as above to give 3-cyclopropylmethyl-1-(p-tolyl)-3-azabicyclo[3.1.0]hexane hydrochloride as colorless crystals, m.p. 180–182° C.

EXAMPLE 16

Preparation of 3-Phenethyl-1-phenyl-3-azabicyclo[3.1.0]hexane hydrochloride

To a stirred solution of 9.35 g of 1-phenyl-1,2-cyclopropanedicarboximide in 50 ml of dimethylformamide is added 2.5 g of sodium hydride (50% in mineral oil) over 5 minutes. This mixture is warmed and stirred for one-half hour, 0.1 g of potassium iodide is added and then 9.25 g of phenethyl bromide is added. This mixture is stirred one-half hour, heated on a steam bath 15 minutes, stirred at room temperature 15 minutes and then poured into one liter of water made acidic with acetic acid. The mixture is extracted with methylene chloride and this solution is combined with 50 g of magnesium silicate and evaporated under reduced pressure. The residual powder is applied to a magnesium silicate column and elution with one liter of petroleum ether, 500 ml of methylene chloride, one liter of chloroform and evaporation produced N-phenethyl-1-phenyl-1,2-cyclopropanedicarboximide as a colorless oil.

To a solution of 5.80 g of the above compound in 50 ml of benzene is added 10 ml of sodium bis(2-methoxyethoxy)aluminum hydride (70% benzene solution) with stirring. The mixture is allowed to stand 18 hours, is refluxed 2 hours, cooled and treated with 10 ml of 10N sodium hydroxide as described in Example 15, yielding the crystalline product, mp 207°–209° C.

EXAMPLE 17

Preparation of 3-Isopropyl-1-phenyl-3-azabicyclo[3.1.0]hexane hydrochloride

A mixture of 20.6 g of 1-phenyl-1,2-cyclopropanedicarboxylic acid and 15 g of 1,3-diisopropylurea in 500 ml of xylene is refluxed for 6 hours, filtered and the solvent removed under reduced pressure giving an oil. The oil is absorbed on magnesium silicate in 500 ml of methylene chloride. The solvent is evaporated leaving a powder. The powder is added to magnesium silicate on a Buchner funnel and eluted with 500 ml of petroleum ether and then one liter of methylene chloride. The methylene chloride is evaporated giving N-isopropyl-1-phenyl-1,2-cyclopropanedicarboximide as a colorless oil.

To a solution of 9.17 g of the above product in 100 ml of benzene is added 20 ml of sodium bis(2-methoxyethoxy)aluminum hydride (70% in benzene) with stirring. The mixture is allowed to stand for 18 hours, is refluxed for 2 hours, cooled and 20 ml of 10N sodium hydroxide is slowly added, followed by 30 ml of 5N sodium hydroxide. The organic layer is extracted with dilute hydrochloric acid. The aqueous extract is made basic with sodium hydroxide, extracted with ether, dried over magnesium sulfate and dry hydrogen chloride gas is bubbled in producing a gum which is triturated with ether and crystallized from acetone yielding tan crystals, mp 141°–144° C.

In a like manner 1-(p-chlorophenyl)-1,2-cyclopropanedicarboxylic acid and 1,3-diphenylurea give N,1-diphenyl-1,2-cyclopropanedicarboximide which is then reduced with sodium bis(2-methoxyethoxy)aluminum hydride (70% in benzene) to give 1,3-diphenyl-3-azabicyclo[3.1.0]hexane.

EXAMPLE 18

Preparation of 1-(p-Trifluoromethylphenyl)-3-azabicyclo[3.1.0]hexane hydrochloride Using the method of Example 6, ethyl p-(trifluoromethyl)phenyl acetate is converted to ethyl α-bromo-p-(trifluoromethyl)phenyl acetate [bp 92°–95° C. (0.4 mm)] and this is reacted with ethyl acrylate-sodium hydride to give diethyl 1-(p-trifluoromethylphenyl)-1,2-cyclopropanedicarboxylate [bp 108°–110° C. (0.2 mm)]. Hydrolysis with 1N potassium hydroxide gives cis-1-(p-trifluoromethylphenyl)-1,2-cyclopropanedicarboxylic acid as colorless crystals, mp 161°–162° C. This diacid is then reacted with urea to give 1-(p-trifluoromethylphenyl)-1,2-cyclopropanedicarboximide as colorless crystals, mp 164°–165° C.

To a solution of 3.5 g of this imide in 75 ml of benzene is added 20 ml of sodium bis(2-methoxyethoxy)aluminum hydride (70% benzene solution). This is refluxed for one hour, cooled to room temperature and the excess hydride reagent is decomposed with 20 ml of 10N sodium hydroxide. The benzene layer is washed with water, dried over magnesium sulfate and evaporated under reduced pressure to give an amber colored oil. This oil is dissolved in ether and dry hydrogen chloride gas is bubbled into the solution. The resultant precipitate is collected by filtration and recrystallized from isopropyl alcohol to give the product, mp 249°–251° C.

EXAMPLE 19

Preparation of
3-(p-Chlorobenzyl)-1-(p-chlorophenyl)-3-azabicyclo[3.1.0]hexane

A 19.35 g sample of 1-p-chlorophenyl-3-azabicyclo[3.1.0]hexane, 10.59 g of sodium carbonate and 17.5 g of p-chlorobenzoyl chloride are reacted in benzene. The benzene is evaporated and the dark purple residue is dissolved in 200 ml of chloroform and washed successively with 5% sodium carbonate, 0.5N hydrochloric acid and then with water and dried over sodium sulfate giving a dark purple oil. Addition of ether gives the product 3-p-chlorobenzoyl-1-(p-chlorophenyl)-3-azabicyclo[3.1.0]hexane as grey crystals, mp 98°–100° C.

A 16.60 g portion of 3-(p-chlorobenzoyl)-1-(p-chlorophenyl)-3-azabicyclo[3.1.0]hexane (prepared above) is dissolved in 160 ml of benzene and 55.5 g of sodium bis(2-methoxyethoxy)aluminum hydride (70% benzene solution) is added dropwise. The mixture is refluxed for 2 hours, cooled and quenched slowly with 10N sodium hydroxide. Water is added, the organic layer is separated and washed 3 times with water and then dried over sodium magnesium sulfate. Removal of the solvent yields an off-white solid, mp 88°–92° C.

In a like manner, reductions of the following amides with sodium bis(2-methoxyethoxy)aluminum hydride yield the corresponding reduced products.

| Amide | Reduction Product |
|---|---|
| A | |
| 3-(2-naphthylcarbonyl)-1-(p-chlorophenyl)-3-azabicyclo[3.1.0]hexane | 3-(2-naphthylmethyl)-1-(p-chlorophenyl)-3-azabicyclo[3.1.0]hexane |
| B | |
| 3-(5-norbornen-2-ylcarbonyl)-1-(p-chlorophenyl)-3-azabicyclo[3.1.0]hexane | 3-(5-norbornen-2-ylmethyl)-1-(p-chlorophenyl)-3-azabicyclo[3.1.0]hexane |
| C | |
| 3-acetyl-1-(p-aminophenyl)-3-azabicyclo[3.1.0]hexane | 3-ethyl-1-(p-aminophenyl)-3-azabicyclo[3.1.0]hexane |
| D | |
| 1-(p-chlorophenyl)-3-propiolyl-3-azabicyclo[3.1.0]hexane | 1-(p-chlorophenyl)-3-propargyl-3-azabicyclo[3.1.0]hexane |

The above intermeidates A, B, and D are prepared by acylation of the corresponding 3-azabicyclo[3.1.0]hexanes with the appropriate acid chloride, as described in Example 19.

The compound 3-acetyl-1-(p-aminophenyl)-3-azabicyclo[3.1.0]hexane is prepared by acetylation of 1-(p-nitrophenyl)-3-azabicyclo[3.1.0]hexane (Example 34), as in Example 19, followed by reduction with palladium on charcoal in tetrahydrofuran.

EXAMPLE 20

Preparation of
3-(1-Adamantylmethyl)-1-(p-chlorophenyl)-3-azabicyclo[3.1.0]hexane A sample of 19.35 g of 1-p-chlorophenyl-3-azabicyclo[3.1.0]hexane, 10.59 g of sodium carbonate and 19.87 g of 1-adamantanecarboxylic acid chloride are reacted in accordance with Example 36, yielding the product 3-(1-adamantylcarbonyl)-1-(p-chlorophenyl)-3-azabicyclo[3.1.0]hexane as a white solid, mp 163°–165° C.

A 17.77 g portion of 3-(1-adamantylcarbonyl)-1-(p-chlorophenyl)-3-azabicyclo[3.1.0]hexane, (prepared above) is treated as described in Example 19 yielding a yellow oil which crystallizes to a white solid on standing, mp 72°–75° C.

EXAMPLE 21

Preparation of
3-Allyl-1-phenyl-3-azabicyclo[3.1.0]hexane hydrochloride

To 18.7 g of 1-phenyl-1,2-cyclopropanedicarboximide in 100 ml of dimethylformamide is added 5 g of sodium hydride (50% in mineral oil). The mixture is warmed on a steam bath and 9 ml of allyl bromide is added over 5 minutes with stirring. This mixture is heated on a steam bath for one-half hour, then at room temperature for 2 hours, poured into one liter of water and extracted with methylene chloride. The organic layer is mixed with 50 g of magnesium silicate and evaporated on a rotary evaporator. This mixture is then added to 200 g of magnesium silicate in a Buchner funnel and eluted with one liter of petroleum ether and then one liter of chloroform. The chloroform fraction is evaporated under reduced pressure giving N-allyl-1-phenyl-1,2-cyclopropanedicarboximide as a colorless oil.

To a solution of 8.0 g of the above product in 70 ml of benzene is added 17.5 ml of sodium bis(2-methoxyethoxy)aluminum hydride (70% benzene solution). The mixture is refluxed for 2 hours and then stirred at room temperature for two hours. Processing as described in Example 19 yields the desired product, mp 124°–128° C.

In a like manner, 1-(p-tolyl)-1,2-cyclopropanedicarboximide (Example 36) is reacted with allyl bromide to give N-allyl-1-(p-tolyl)-1,2-cyclopropanedicarboximide which is then reduced as above to give 3-allyl-1-(p-tolyl)-3-azabicyclo[3.1.0]hexane hydrochloride as colorless crystals, m.p. 165°–167° C.

In a like manner, 1-(p-tolyl)-1,2-cyclopropanedicarboximide (Example 36) is reacted with propargyl bromide to give N-propargyl-1-(p-tolyl)-1,2-azacyclopropanedicarboximide which is then reduced as above to give 3-propargyl-1-(p-tolyl)-3-azabicyclo[3.1.0]hexane hydrochloride.

EXAMPLE 22

Preparation of
3-Ethyl-1-phenyl-3-azabicyclo[3.1.0]hexane hydrochloride

To 15.9 g of 1-phenyl-3-azabicyclo[3.1.0]hexane in 20 ml of pyridine is added 20 ml of acetic anhydride. The mixture is allowed to stand overnight at room temperature and then evaporated to give an oil. This oil is dissolved in a mixture of ether and methylene chloride, washed with dilute hydrochloric acid and then sodium bicarbonate and dried over magnesium sulfate and evaporated to a pale amber liquid. This liquid is crystallized from hexane to give the product 3-acetyl-1-phenyl-3-azabicyclo[3.1.0]hexane mp 63°–65° C.

A 10.0 g portion of 3-acetyl-1-phenyl-3-azabicyclo[3.1.0]hexane, prepared above, in 100 ml of benzene is treated with 25 ml of sodium bis(2-methoxyethoxy)aluminum hydride (70% benzene solution) as described in Example 19, yielding tan crystals, mp 148°–152° C.

EXAMPLE 23

Preparation of 3-(Cyclohexylmethyl)-1-phenylazabicyclo[3.1.0]hexane hydrochloride A 6.4 g portion of 1-phenyl-3-azabicyclo[3.1.0]hexane is added to 60 ml of benzene. A 4.2 g portion of sodium carbonate in 40 ml of water is added with stirring. A 5.9 g portion of cyclohexylcarbonyl chloride in 40 ml of benzene is added and the mixture is stirred overnight. The oily solid in the aqueous layer is extracted with chloroform. The extracts are washed with water and dilute hydrochloric acid, dried over magnesium sulfate, filtered and evaporated. The oily residue is extracted with ether giving a white solid as the product 3-cyclohexylcarbonyl-1-phenyl-3-azabicyclo[3.1.0]hexane, mp 81°–82° C.

A 7.0 g portion of 3-cyclohexylcarbonyl-1-phenyl-3-azabicyclo[3.1.0]hexane, prepared above in 50 ml of benzene is treated with 13 ml of sodium bis(2-methoxyethoxy)aluminum hydride (70% benzene solution) and 13 ml of 10N sodium hydroxide, as described in Example 19, yielding the hydrochloride as colorless crystals, mp 215°–218° C.

EXAMPLE 24

Preparation of 1-(p-Methoxyphenyl)-3-azabicyclo[3.1.0]hexane hydrochloride

A mixture of 2.6 g of diethyl 1-(p-methoxyphenyl)-1,2-cyclopropanedicarboxylate (prepared by the method of Example 6 from ethyl-p-methoxyphenylacetate), 20 ml of 1N potassium hydroxide and 20 ml of ethanol is refluxed 3.5 hours and the ethanol is removed by concentrating. A 20 ml portion of 1N hydrochloric acid is added and then incremental portions of acid are added until the pH is one. The mixture is extracted three times with chloroform, dried and concentrated to a yellow solid. This solid is recrystallized from ethyl acetate-hexane to give cis-1-(p-methoxyphenyl)-1,2-cyclopropanedicarboxylic acid as a pale yellow solid.

A 6.6 g portion of this diacid, 2.4 g of urea and 300 ml of xylene is refluxed and stirred for 24 hours. The mixture is cooled, diluted with 25 ml of benzene, washed with water, dried, concentrated under reduced pressure to give a solid which is recrystallized from ethyl acetate-hexane to give 1-(p-methoxyphenyl)-1,2-cyclopropanedicarboximide.

A 3.0 g portion of the above product is mixed with 70 ml of benzene and 20 ml of sodium bis(2-methoxyethoxy)aluminum hydride (70% benzene solution) is added over a 5 minute period with stirring. After stirring for one-half hour and refluxing for one hour the mixture is cooled and 20 ml of 10N sodium hydroxide is added followed by saturated sodium chloride. The organic layer is dried over magnesium sulfate, filtered and evaporated to an oil. The oil is dissolved in ether and hydrogen chloride gas is bubbled in. The solid which forms is recrystallized from isopropyl alcohol giving pale pink plates, mp 174°–175° C.

EXAMPLE 25

Preparation of (+)-1-Phenyl-3-azabicyclo[3.1.0]hexane hydrochloride

To a stirred slurry of 10 g of (+)-1-phenyl-1,2-cyclopropanedicarboximide in 300 ml of benzene under nitrogen is added 80 ml of sodium bis(2-methoxyethoxy)aluminum hydride (70% benzene solution). The mixture is stirred at room temperature for 2 hours, refluxed for 4 hours, stirred at room temperature for 20 hours and then 80 ml of 10N sodium hydroxide is added slowly with stirring. The organic layer is washed with saturated sodium chloride, water, dried over magnesium sulfate and filtered. The filtrate is evaporated, ether is added and dry hydrogen chloride gas is bubbled in. The product is recovered by filtration and recrystallized from acetonitrile giving colorless needles, mp 169°–171° C., $[\alpha]_D^{CH_3OH} = +68°$ C.

EXAMPLE 26

Preparation of 1-(p-Chlorophenyl)-3-(o-fluorobenzyl)-3-azabicyclo[3.1.0]hexane hydrochloride A sample of 19.53 g of 1-(p-chlorophenyl)-3-azabicyclo[3.1.0]hexane, 10.59 g of sodium carbonate and 15.8 g of o-fluorobenzoyl chloride are reacted to give the product 3-(o-fluorobenzoyl)-1-(p-chlorophenyl)-3-azabicyclo[3.1.0]hexane as a brown gum.

A 13.9 g portion of 3-(o-fluorobenzoyl)-1-(p-chlorophenyl)-3-azabicyclo[3.1.0]hexane is reacted as described in Example 19 with 50 ml of sodium bis(2-methoxyethoxy)aluminum hydride (70% benzene solution) yielding a light yellow oil. This base is treated with ethanolic hydrochloric acid and ether to give the hydrochloride as a white solid, mp 204°–206° C.

In a similar manner, 3-(p-fluorobenzoyl)-1-phenyl-3-azabicyclo[3.1.0]hexane is reduced by sodium bis(2-methoxyethoxy)aluminum hydride to give 3-(p-fluorobenzyl)-1-phenyl-3-azabicyclo[3.1.0]hexane.

Likewise, 3-(m-fluorobenzoyl)-1-phenyl-3-azabicyclo[3.1.0]hexane is converted to 3-(m-fluorobenzyl)-1-phenyl-3-azabicyclo[3.1.0]hexane.

EXAMPLE 27

Preparation of 1-(3,4-Dichlorophenyl)-3-azabicyclo[3.1.0]hexane

A solution of 59.5 g of 3,4-dichlorophenylacetic acid in 500 ml of absolute ethanol is saturated with anhydrous hydrogen chloride and then heated at reflux for 2 hours. The mixture is concentrated under reduced pressure to 200 ml, diluted with 200 ml of water and neutralized with concentrated ammonium hydroxide. This aqueous mixture is extracted 3 times with chloroform. Concentration and decolorization of the chloroform extracts gives ethyl 3,4-dichlorophenylacetate as a yellow oil.

In a three-necked flask fitted with a Nichrome stirrer and a reflux condenser is placed 7.0 g of ethyl 3,4-dichlorophenylacetate, 5.9 g of N-bromosuccinimide, 0.1 g of benzoyl peroxide and 150 ml of carbon tetrachloride. The reaction mixture is heated at reflux for 18 hours, cooled and filtered. The carbon tetrachloride filtrate is concentrated under reduced pressure to give a deep orange liquid. Vacuum distillation at 115°–120° C. (0.5 mm) gives ethyl α-bromo-3,4-dichlorophenylacetate as a pale yellow liquid.

This product is converted to diethyl cis-1-(3,4-dichlorophenyl)-1,2-cyclopropanedicarboxylate by the method of L. L. McCoy, J. A. C. S., 80, 6568 (1958).

A mixture of 150 g of this diester and 66 g of 85% KOH in 500 ml of water and 500 ml of ethanol is refluxed for 6 hours and then chilled in ice. The oily material is extracted into ether and the aqueous layer is made acidic with 100 ml of 12N hydrochloric acid. The oily lower layer crystallizes slowly to give a colorless crystalline cake. This is recrystallized from a mixture of ethanol and ethyl acetate to give colorless crystals of 1-(3,4-dichlorophenyl)-1,2-cyclopropanedicarboxylic acid.

A mixture of 30.3 g of this diacid and 12.6 g of urea in one liter of xylene is refluxed for 6 hours. The solvent is stripped under reduced pressure and the crystalline residue is slurried with water. The colorless crystals are collected by filtration, washed with water and air dried to give 1-(3,4-dichlorophenyl)-1,2-cyclopropanedicarboximide.

To 40 ml of 1 molar borane-tetrahydrofuran is added with stirring under nitrogen at 0° C. a solution of 2.56 g of this imide in 50 ml of tetrahydrofuran during 15 minutes. The solution is warmed in a steam bath for 1 hour and is then cooled in ice, and then 20 ml of 6N hydrochloric acid is added, and the tetrahydrofuran is removed under reduced pressure. The residue is made basic with 75 ml of 5N sodium hydroxide and this is extracted with ether. The extract is dried over magnesium sulfate, filtered, and the filtrate is saturated with hydrogen chloride. The precipitated crystals are collected by filtration and are recrystallized from isopropyl alcohol to give 1.70 g of 1-(3,4-dichlorophenyl)-3-azabicyclo[3.1.0]hexane hydrochloride as colorless crystals, m.p. 180°–181° C.

The following imides, prepared in the above manner, are likewise reduced to the corresponding 3-azabicyclo[3.1.0]hexanes:

| Imide | Reduction Product |
| --- | --- |
| 1-(p-ethylphenyl)-1,2-cyclopropanedicarboximide, m.p. 102°–104° C. | 1-(p-ethylphenyl)-3-azabicyclo[3.1.0]hexane hydrochloride, m.p. 207°–209° C. |
| 1-(p-hexylphenyl)-1,2-cyclopropanedicarboximide, m.p. 115°–117° C. | 1-(p-hexylphenyl)-3-azabicyclo[3.1.0]hexane hydrochloride, m.p. 181°–183° C. |
| 1-(m-tolyl)-1,2-cyclopropanedicarboximide, m.p. 164°–166° C. | 1-(m-tolyl)-3-azabicyclo[3.1.0]hexane hydrochloride, m.p. 129°–131° C. |
| 1-(p-bromophenyl)-1,2-cyclopropanedicarboximide, m.p. 150°–151° C. | 1-(p-bromophenyl)-3-azabicyclo[3.1.0]hexane hydrochloride, m.p. 231°–233° C. |
| 1-(p-fluorophenyl)-1,2-cyclopropanedicarboximide, m.p. 146°–148° C. | 1-(p-fluorophenyl)-3-azabicyclo[3.1.0]hexane hydrochloride, m.p. 170°–172° C. |

In the above manner, N-benzoyl-1-(p-bromophenyl)-1,2-cyclopropanedicarboximide, made by reaction of 1-(p-bromophenyl)-1,2-cyclopropanedicarboximide with benzyl chloride, as in Example 14, is converted to 3-benzyl-1-(p-bromophenyl)-3-azabicyclo[3.1.0]hexane, m.p. 69°–70° C.

EXAMPLE 28

Preparation of 1-(m-Methoxyphenyl)-3-methyl-3-azabicyclo[3.1.0]hexane hydrochloride A 92.3 g portion of m-anisidine is dissolved in 225 ml of concentrated hydrochloric acid, 150 ml of water and 150 g of ice and cooled to 0° C. This mixture is diazotized carefully with vigorous stirring at 0°–5° C. with 52.5 g of sodium nitrite in 120 ml of water. This mixture is then added to 83.25 g of N-methylmaleimide in 225 ml of acetone at 0° C. The pH is adjusted to 3.0 and 25.5 g of cuprous chloride dihydrate is added in one portion followed by 200 ml of acetone, with stirring. Evaporation of the acetone and decantation of the aqueous layer leaves a black residue which is boiled with one liter of benzene, dried over magnesium sulfate and filtered through a Buchner funnel containing 50 g of activated magnesium silicate. The residue is boiled with one liter of benzene and filtered through activated magnesium silicate. The dark filtrate is evaporated under reduced pressure and then heated for 10 minutes with 100 ml of 2,6-lutidine to insure dehydrochlorination. This solution is combined with 500 ml of water and 400 ml of pyridine and filtered. The crystalline cake is pressed free of dark oil and then boiled with 500 ml of 90% ethanol. This is cooled and filtered giving 2-(m-methoxyphenyl)-N-methylmaleimide as orange crystals, m.p. 138°–146° C.

This product is converted to 1-(m-methoxyphenyl)-N-methyl-1,2-cyclopropanedicarboximide by the method of P. T. Izzo, J. Organic Chemistry, 28, 1713 (1963).

To a mixture of 3.0 g of this imide in 70 ml of benzene is added 20 ml of sodium bis(2-methoxyethoxy)aluminum hydride (70% benzene solution) over a 5 minute period under nitrogen with stirring. The mixture is stirred for 30 minutes, refluxed for one hour, cooled and 20 ml of 10N sodium hydroxide and then saturated sodium chloride are added. The organic layer is dried over magnesium sulfate, filtered and evaporated giving crystals which are recrystallized from ether. Reaction with hydrogen chloride gas and recrystallization form isopropyl alcohol gives the crystalline product 1-(m-methoxyphenyl)-3-methyl-3-azabicyclo[3.1.0]hexane hydrochloride, mp 148°–150° C.

EXAMPLE 29

Preparation of (+)-1-Phenyl-3-methyl-3-azabicyclo[3.1.0]hexane hydrochloride

A mixture of 10 g of (+)-1-phenyl-1,2-cyclopropanedicarboximide, 2.67 g of sodium hydride (50% in mineral oil), 50 ml of dimethylformamide and 5 ml of methyl iodide is reacted and poured into 500 ml of water. This mixture is extracted with methylene chloride, washed with water, dried over magnesium sulfate, and evaporated. The residue is adsorbed on activated magnesium silicate in a Buchner funnel and washed with 250 ml of benzene. The eluate is washed with 500 ml of methylene chloride and evaporated giving green crystals of (+)-1-phenyl-N-methyl-1,2-cyclopropanedicarboximide.

A 3.0 g portion of this imide in 70 ml of dry benzene is reacted with 20 ml of sodium bis(2-methoxyethoxy)aluminum hydride (70% benzene solution). The mixture is stirred for 15 minutes at room temperature and then on a steam bath for 15 minutes. After cooling the reaction mixture is treated as described in Example 12 giving (+)-1-phenyl-3-methyl-3-azabicyclo[3.1.0]hexane hydrochloride as crystals, mp 188°–190° C., $[\alpha]_D^{C-H_3OH} = +72°$.

EXAMPLE 30

Preparation of 1-(4-Chloro-α,α,α-trifluoro-m-tolyl)-3-azabicyclo[3.1.0]hexane hydrochloride Using the method of Example 6, methyl(4-chloro-α,α,α-trifluoro-m-tolyl)acetate is converted to methyl bromo(4-chloro-α,α,α-trifluoro-m-tolyl)acetate, and this is reacted with methyl acrylate-sodium hydride to give dimethyl 1-(4-chloro-α,α,α-trifluoro-m-tolyl)cyclopropanedicarboxylate. Hydrolysis with 1N potassium hydroxide gives cis-1-(4-chloro-α,α,α-trifluoro-m-tolyl)-1,2-cyclopropanedicarboxylic acid as colorless crystals, mp 167°–169° C., and the diacid is then reacted with urea to give 1-(4-chloro-α,α,α-trifluoro-m-tolyl)-1,2-cyclopropanedicarboximide as colorless crystals, mp 123°–124° C.

To a solution of 0.28 g of 1-(4-chloro-α,α,α-trifluoro-m-tolyl)cyclopropanedicarboximide in 10 ml of benzene is added 1.0 ml of sodium bis(2-methoxyethoxy)aluminum hydride (70% benzene solution). This is refluxed for one hour, cooled to ambient temperature, and the excess hydride reagent is decomposed with one ml of 10N sodium hydroxide. The benzene layer is washed with water, dried over magnesium sulfate and evaporated under reduced pressure to give an amber-colored oil. This is dissolved in ether and dry hydrogen chloride is bubbled into the solution. The resultant precipitate is collected by filtration and recrystallized from isopropyl alcohol to give 1-(4-chloro-α,α,α-trifluoro-m-tolyl)-3-azabicyclo[3.1.0]hexane hydrochloride. Purification of the hydrochloride by recrystallization from acetonitrile gives colorless crystals, m.p. 164°–166° C.

EXAMPLE 31

Preparation of 3,6-Dimethyl-1-phenyl-3-azabicyclo[3.1.0]hexane hydrochloride

To a stirred solution of N, 3-dimethylcyclopropane-1,2-dicarboximide (U.S. Pat. No. 3,166,571, Ex. 2) in benzene is added sodium bis(2-methoxyethoxy)aluminum hydride (70% benzene solution) for several minutes. This solution is stirred at ambient temperature for several hours, refluxed for one hour, and then cooled and combined with sodium hydroxide and worked-up and converted to the hydrochloride as described in Example 11 to give the title product.

EXAMPLE 32

Preparation of 1-(p-Acetamidophenyl)-3-ethyl-3-azabicyclo[3.1.0]hexane

To a suspension of 3-ethyl-1-(p-aminophenyl)-3-azabicyclo[3.1.0]hexane (Example 19) in aqueous sodium acetate is added acetic anhydride. This is heated on a steam bath for several minutes and filtered to give the product.

EXAMPLE 33

Preparation of 1-(m-Hydroxyphenyl)-3-methyl-3-azabicyclo[3.1.0]hexane

A solution of 1-(m-methoxyphenyl)-3-methyl-3-azabicyclo[3.1.0]hexane in 48% hydrobromic acid is refluxed for several hours and the solution is made basic with sodium bicarbonate. The desired phenol is collected by filtration.

EXAMPLE 34

Preparation of 1-(p-Nitrophenyl)-3-azabicyclo[3.1.0]hexane hydrochloride

To a stirred slurry of 20.6 g of 1-phenylcyclopropane-1,2-dicarboxylic acid in 25 ml of concentrated sulfuric acid at 0° C. is added 15 ml of concentrated nitric acid over 30 minutes. The resultant solution is then stirred at ambient tmperature for 30 minutes and then poured onto ice. The crystalline product is recrystallized from hexane-ethyl acetate to give 1-(p-nitrophenyl)-cyclopropane-1,2-dicarboxylic acid as colorless crystals, m.p. 138°–144° C.

The above diacid is converted to 1-(p-nitrophenyl)-1,2-cyclopropane-dicarboximide, m.p. 171°–173° C., by the method described in Example 6.

A solution of the above imide in tetrahydrofuran is added to a 1M solution of borane-tetrahydrofuran at 0° C., under nitrogen. The solution is refluxed for one hour, cooled to 0° C. and then 6N hydrochloric acid is added. Tetrahydrofuran is removed under reduced pressure and the residual material is distributed between ether and sodium hydroxide. The ether solution, containing 1-(p-nitrophenyl)-3-azabicyclo[3.1.0]hexane, is dried over magnesium sulfate and filtered, and to the filtrate is added hydrogen chloride to give the product as a brown solid, m.p. 215°–217° C.

EXAMPLE 35

Preparation of 1-(o-Chlorophenyl)-3-azabicyclo[3.1.0]hexane hydrochloride

A stirred mixture of 36.9 g of methyl o-chlorophenylacetate, 36.0 g of N-bromosuccinimide, and 2 drops of 48% hydrobromic acid in 500 ml of carbon tetrachloride is refluxed for 20 hours and then filtered through magnesium silicate. Evaporation under reduced pressure gives methyl α-bromo-o-chlorophenylacetate as a straw-colored liquid.

To a stirred suspension of 4.8 g of sodium hydride (50% in mineral oil) in 100 ml of benzene-N,N-dimethylformamide (1:1) is added a mixture of 26.3 g of the above bromoester and 8.69 g of methyl acrylate over ½ hour. The mixture is stirred at ambient temperature for 4 hours, excess sodium hydride is then decomposed with 2 ml of methanol, and this mixture is poured into 500 ml of water. The organic layer is washed with water, dried over magnesium sulfate, and evaporated to give dimethyl-1-(o-chlorophenyl)-1,2-cyclopropanedicarboxylate as a brown oil.

The above diester (17.35 g) and 200 ml of 1N potassium hydroxide in 50 ml of ethanol is refluxed for 6 hours. The solution is reduced to one-half volume under reduced pressure and acidified to give 1-(o-chlorophenyl)-1,2-cyclopropanedicarboxylic acid as a brown oil.

A mixture of 10.0 g of the above diacid and 3.4 g of urea in 500 ml of xylene is refluxed for 6 hours. The solution is washed with water and sodium bicarbonate and then dried over magnesium sulfate to give a tan solid. Recrystallization from ethanol gives 1-(o-chlorophenyl)-1,2-cyclopropanedicarboximide as colorless crystals, mp 154°–156° C.

To 1.35 g of the above imide in 30 ml of benzene is added 9 ml of sodium bis(2-methoxyethoxy)aluminum hydride (70% benzene solution) over 2 minutes with stirring. The solution is stirred at ambient temperature for 15 minutes and is then refluxed for 30 minutes. To the cooled solution is added 10 ml of 10N sodium hydroxide and the benzene layer is washed with water, dried over magnesium sulfate and filtered. The filtrate is evaporated under reduced pressure and the residual oil is dissolved in ether and to this solution is added anhydrous hydrogen chloride gas. The precipitated product is recrystallized from isopropyl alcohol to give 1-(o-chlorophenyl)-3-azabicyclo[3.1.0]hexane hydrochloride as colorless crystals, mp 188°–190° C.

EXAMPLE 36

Preparation of 1-(p-tolyl)-3-azabicyclo[3.1.0]hexane hydrochloride

To 120 g of p-tolylacetic acid is added 230 ml of thionyl chloride and the solution is allowed to stand at room temperature for 2 hours, after which it is warmed to 60° C. for 1 hour. To this solution is added 285 g of N-bromosuccinimide and 10 drops of 48% hydrobromic acid and the mixture is then refluxed on a 90° C. oil bath for 1 hour. An additional 90 ml of thionyl chloride is added and refluxing continued for 45 minutes. The mixture is distilled under reduced pressure to remove 250 ml of thionyl chloride, and the residual liquid is poured into 500 ml of cold methanol with stirring and ice cooling over 15 minutes. This solution is evaporated under reduced pressure to give a dark oil which is dissolved in 100 ml of chloroform. The solution is washed with 500 ml of water, dried over magnesium sulfate and filtered. The filtrate is evaporated under reduced pressure to give a dark oil which is distilled to give 94 g of bromoester as a pale yellow liquid, bp. 115°–120° C. (0.05 mm). The pale yellow liquid is then reacted with methyl acrylate-sodium hydride in ether (as in Example 6) to give dimethyl cis-1-(p-tolyl)-1,2-cyclopropanedicarboxylate, mp 58°–59° C. Hydrolysis with 1N potassium hydroxide, followed by acidification with hydrochloric acid (as in Example 6), gives cis-1-(p-tolyl)-1,2-cyclopropanedicarboxylic acid as colorless crystals, mp 188°–190° C. This diacid is then reacted with urea (as in Example 6) to give 1-(p-tolyl)-1,2-cyclopropanedicarboximide as pale yellow crystals, mp 82°–85° C.

To a mixture of 20.1 g of this imide in 600 ml of benzene is added 160 ml of sodium bis(2-methoxyethoxy)aluminum hydride and the reaction is run as in Example 8 and then the excess reagent is decomposed with 160 ml of 10N sodium hydroxide. The benzene layer is washed with water, dried over magnesium sulfate and filtered. The filtrate is evaporated under reduced pressure to give a dark oil which is dissolved in ether, and then dry hydrogen chloride is bubbled into the solution. The resultant precipitate is collected by filtration and recrystallized from acetonitrile-methanol to give 12.1 g of 1-(p-tolyl)-3-azabicyclo[3.1.0]hexane hydrochloride as pale tan plates, mp 207°–208° C.

In the same manner as described in the above example, 1-(p-cumyl)-1,2-cyclopropanedicarboximide, m.p. 147°–148° C. gives 1-(p-cumyl)-3-azabicyclo[3.1.0]hexane hydrochloride, m.p. 231°–232° C.

The following imides are reduced in the above manner to give the corresponding amine hydrochloride:

| Imide | 3-Azabicyclo[3.1.0]hexane |
|---|---|
| 1-(α,α,α-trifluoro-m-tolyl)-1,2-cyclopropanedicarboximide, m.p. 94°–95.5° C. | 1-(α,α,α-trifluoro-m-tolyl)-3-azabicyclo[3.1.0]hexane hydrochloride, m.p. 146°–148° C. |
| 1-(3-bromo-4-methoxyphenyl)-1,2-azacyclopropanedicarboximide, m.p. 184°–186° C. | 1-(3-bromo-4-methoxyphenyl)-3-azabicyclo[3.1.0]hexane hydrochloride, m.p. 108°–211° C. |
| 1-(o-tolyl)-1,2-cyclopropanedicarboximide | 1-(o-tolyl)-3-azabicyclo[3.1.0]hexane hydrochloride |
| 1-(p-cyclohexylphenyl)-1,2-cyclopropanedicarboximide | 1-(p-cyclohexylphenyl)-3-azabicyclo[3.1.0]hexane |
| 1-(4-biphenyl)-1,2-cyclopropanedicarboximide | 1-(4-biphenyl)-3-azabicyclo[3.1.0]hexane |

EXAMPLE 37

Preparation of (+)-1-(p-Tolyl)-3-azabicyclo[3.1.0]hexane hydrochloride

A solution of 94.8 g of racemic-1-(p-tolyl)-1,2-cyclopropanedicarboxylic acid (Example 36) and 73.8 g of (−)-α-(1-naphthyl)ethylamine in 300 ml of tetrahydrofuran is diluted with 300 ml of ethyl ether and is allowed to stand at room temperature until crystallization is complete. The mixture is filtered and the crystals which are collected are washed with cold tetrahydrofuran to give 4.95 g of a salt comprised of one molar equivalent of (+)-1-(p-tolyl)-1,2-cyclopropanedicarboxylic acid and one molar equivalent of (−)-α-(1-naphthyl)ethylamine. The salt is shaken with sodium hydroxide solution and ether. The aqueous phase is acidified with 12N hydrochloric acid and the product is collected by filtration to give 26.0 g of (+)-1-(p-tolyl)-1,2-cyclopropanedicarboxylic acid as colorless crystals, $[\alpha]_D^{CH_3OH} = +192°$.

A 15.0 g portion of (+)-1-(p-tolyl)-1,2-cyclopropanedicarboxylic acid, 6.6 g of urea and 500 ml of xylene is refluxed and stirred for 5 hours. The reaction mixture is then filtered hot and the filtrate is evaporated under reduced pressure to give (+)-1-(p-tolyl)-1,2-cyclopropanedicarboximide as colorless crystals, m.p. 148°–155° C.

A 14 g portion of the above product is mixed with 420 ml of benzene and 112 ml of sodium bis(2-methoxyethoxy)aluminum hydride (70% benzene solution) is added over a 15 minute period with stirring. After refluxing for 1½ hours the mixture is cooled and 160 ml of 10N sodium hydroxide is added. The organic layer is dried over sodium sulfate, filtered and evaporated to an oil. The oil is dissolved in ether and hydrogen chloride gas is bubbled in. The solid which forms is recrystallized from acetonitrile giving (+)-1-(p-tolyl)-3-azabicyclo[3.1.0]hexane hydrochloride as colorless crystals, m.p. 208°–210.5° C., $[\alpha]_D^{CH_3OH} = +64.5°$.

The above racemic-diacid is combined with an equimolar amount of brucine in ethanol to give a salt comprised of one molar equivalent of (−)-1-(p-tolyl)-1,2-cyclopropanedicarboxylic acid and one molar equivalent of brucine, $[\alpha]_D^{CH_3OH} = -46°$. Treatment of this salt, as above, gives (−)-1-(p-tolyl)-1,2-cyclopropanedicarboxylic acid as colorless crystals, $[\alpha]_D^{CH_3OH} = -189°$.

In the above manner, (−)-1-(p-tolyl)-1,2-cyclopropanedicarboxylic acid is converted to (−)-1-(p-tolyl)-1,2-cyclopropanedicarboximide, m.p. 145°–148° C., $[\alpha]_D^{CH_3OH} = -74°$. and this is then reduced as above to give (−)-1-(p-tolyl)-3-azabicyclo[3.1.0]hexane hydrochloride as colorless crystals, m.p. 204°–207° C., $[\alpha]_D^{CH_3OH} = -64°$.

EXAMPLE 38

Preparation of 3-Methyl-1-(p-tolyl-3-azabicyclo[3.1.0]hexane hydrochloride

A mixture of 4.19 g of 1-(p-tolyl)-3-azabicyclo[3.1.0]hexane hydrochloride and 20 ml of water is made basic with sodium hydroxide, and this mixture is extracted with ether and the ether is evaporated to give an oil. This oil is combined with 40 ml of 97% formic acid and 35 ml of 37% formaldehyde and the solution is heated on a steam bath for 2 hours. The solution is cooled, made basic with sodium hydroxide and extracted with ether. The extract is dried over magnesium sulfate, filtered, and the filtrate is saturated with hydrogen chloride. The precipitated crystals are collected and recrystallized from isopropyl alcohol to give 3-methyl-3-azabicyclo[3.1.0]hexane hydrochloride as colorless crystals, m.p. 197°–198° C.

The following amines can also be converted to the N-methyl derivative in the above manner.

| Amine | N-Methyl Derivative |
| --- | --- |
| (+)-1-(p-tolyl)-3-azabicyclo-[3.1.0]hexane | (+)-3-methyl-1-(p-tolyl)-3-azabicyclo[3.1.0]hexane |
| (−)-1-(p-tolyl)-3-azabicyclo-[3.1.0]hexane | (−)-3-methyl-1-(p-tolyl)-3-azabicyclo[3.1.0]hexane |

EXAMPLE 39

Preparation of 1-(p-Hydroxyphenyl)-3-azabicyclo[3.1.0]hexane hydrochloride

To a slurry of 7.2 g (0.15 mol) of sodium hydride (50% oil dispersion) in 170 ml of N,N-dimethylformamide at 0°–5° is added a solution of 10.1 ml of ethanethiol in 85 ml of N,N-dimethylformamide over a 15 minute period. An additional 3.16 g portion of sodium hydride is added followed by 14.4 g of 1-(p-methoxyphenyl)-3-azabicyclo[3.1.0]hexane hydrochloride. After the addition of 40 ml of N,N-dimethylformamide, the mixture is refluxed for 4 hours and the solvent is then removed. The residue is dissolved in 150 ml of water and mineral oil is extracted with ether. The aqueous solution is made acidic with acetic acid and the precipitated crystals are collected by filtration to give 9.8 g of 3-formyl-1-(p-hydroxyphenyl)-3-azabicyclo[3.1.0]hexane as tan crystals, m.p. 166°–167°.

A solution of 4.50 g of the above N-formyl derivative in 40 ml of 1.25N sodium hydroxide is heated on a steam bath for 3 hours under nitrogen. The chilled solution is neutralized with acetic acid and filtered to give 3.30 g of the amine as a tan powder, m.p. 174°–177°. This is dissolved in 20 ml of abs. ethanol and HCl gas is bubbled into the solution. Evaporation of the liquid gives 3.78 g of (p-hydroxyphenyl)-3-azabicyclo[3.1.0]hexane hydrochloride as tan crystals, m.p. 195°–196°.

EXAMPLE 40

Preparation of 1-(m-Hydroxyphenyl)-3-azabicyclo[3.1.0]hexane hydrochloride

In the manner of Example 39, 1-(m-methoxyphenyl)-3-azabicyclo[3.1.0]hexane hydrochloride is converted to 3-formyl-1-(m-hydroxyphenyl)-3-azabicyclo[3.1.0]hexane, m.p. 129°–130° C. This is hydrolyzed with sodium hydroxide, as described above, to give 1-(m-hydroxyphenyl)-3-azabicyclo[3.1.0]hexane hydrochloride as pale tan crystals, m.p. 209°–210° C.

EXAMPLE 41

Preparation of 1-(p-Ethoxyphenyl)-3-azabicyclo[3.1.0]hexane hydrochloride

To a stirred mixture of 1.0 g of 3-formyl-1-(p-hydroxyphenyl)-3-azabicyclo[3.1.0]hexane and 0.7 g of potassium carbonate in 25 ml of absolute ethanol is added a solution of 3.2 g of ethyl iodide in 10 ml of absolute ethanol. The mixture is refluxed for 2 hours and then is filtered and evaporated. The residual mixture of crystals and liquid is combined with water and this is extracted with chloroform and the extract is dried over magnesium sulfate and evaporated to give 1.0 g of a colorless, viscous liquid, which crystallizes on standing. Recrystallization from hexane gives 0.31 g of 3-formyl-1-(p-ethoxyphenyl)-3-azabicyclo[3.1.0]hexane as colorless crystals, m.p. 48°–51° C.

A solution of 2.0 g of this compound in 50 ml of ethanol and 20 ml of 5N sodium hydroxide is heated on a steam bath for 30 minutes and the ethanol is then removed under reduced pressure. The residue is extracted with ether and the extract is dried over magnesium sulfate, filtered, and then is evaporated to give 1-(p-ethoxyphenyl)-3-azabicyclo[3.1.0]hexane as colorless crystals, m.p. 48°–49° C. This is combined with ethanolic hydrogen chloride to give 1-(p-ethoxyphenyl)-3-azabicyclo[3.1.0]hexane hydrochloride as colorless crystals, m.p. 192°–193° C.

EXAMPLE 42

Preparation of 1-Phenyl-3-azabicyclo[3.1.0]hexane hydrochloride

A solution of 9.00 g of cis-1-phenyl-1,2-cyclopropanedicarboxylic acid in 100 ml of tetrahydrofuran is added to 180 ml of 1M borane-tetrahydrofuran at 0° C., under nitrogen over 15 minutes. The solution is kept at room temperature for 30 minutes and then is refluxed for 4 hours. After cooling the reaction mixture in ice, 60 ml of 6N hydrochloric acid is added and the tetrahydrofuran is removed under reduced pressure. The aqueous residue is made basic with sodium hydroxide and extracted with ether. The extract is dried over potassium carbonate and the filtered solution is evaporated to give 7.7 g of cis-1-phenyl-1,2-cyclopropanedimethanol.

A solution of 6.00 g of the above diol in 335 ml of dichloromethane and 14 ml of triethylamine is cooled to −10° C. and to this is added 8.45 g of methanesulfonyl chloride over 15 minutes. This is stirred at room temperature for 30 minutes and is then washed with cold dilute hydrochloric acid, then with cold water and finally with 10% sodium bicarbonate solution. The organic solution is dried over magnesium sulfate, and the filtered solution is evaporated to give 8.40 g of the dimethanesulfonate as a pale yellow oil. A solution of this oil in 100 ml of tetrahydrofuran is combined with 1.0 g of sodamide and this mixture is refluxed and filtered. Evaporation of the solution gives 1-phenyl-3-azabicyclo[3.1.0]hexane as a colorless liquid. Conversion of this amine to the hydrochloride with ethanolic hydrogen chloride gives 1-phenyl-3-azabicyclo[3.1.0]hexane hydrochloride. When recrystallized from acetonitrile, the product is obtained as colorless crystals, m.p. 166°–167° C.

EXAMPLE 43

Preparation of 1-(m-Chlorophenyl)-3-methyl-3-azabicyclo[3.1.0]hexane hydrochloride By the method of Example 10, 1-(m-chlorophenyl)-N-methyl-1,2-cyclopropanedicarboximide, m.p. 72°–73° C., prepared from 1-(m-chlorophenyl)-1,2-cyclopropanedicarboximide (Example 6) and methyl iodide gives 1-(m-chlorophenyl)-3-methyl-3-azabicyclo[3.1.0]hexane hydrochloride as colorless crystals, m.p. 180°–182° C.

EXAMPLE 44

Preparation of
1-(p-Chlorophenyl)-3-ethyl-3-azabicyclo[3.1.0]hexane

Using the method of Example 19, 1-(p-chlorophenyl)-3-azabicyclo[3.1.0]hexane (Example 1) is reacted with acetyl chloride to give 3-acetyl-1-(p-chlorophenyl)-3-azabicyclo[3.1.0]hexane and then is converted to 1-(p-chlorophenyl)-3-ethyl-3-azabicyclo[3.1.0]hexane which is obtained as a brown oil.

EXAMPLE 45

Preparation of
3-[4,4-bis(p-Fluorophenyl)butyl]-1-phenyl-3-azabicyclo[3.1.0]hexane Fumarate A mixture of sodium hydride and 1-phenyl-1,2-cyclopropanedicarboximide (U.S. Pat. No. 3,166,571) in dry N,N-dimethylformamide is stirred until hydrogen evolution ceases. To this is added 1-chloro-4,4-bis(4-fluorophenyl)butane and the mixture is stirred for 20 hours at room temperature and then is heated briefly at 100° C. The mixture is combined with water and extracted with ether and the extract is evaporated to give N-[4,4-bis(p-fluorophenyl)butyl]-1-phenyl-1,2-cyclopropanedicarboximide as a colorless glass.

Reduction of the above compound as in Example 10 and the combination of the base with fumaric acid gives 3-[4,4-bis(p-fluorophenyl)butyl]-1-phenyl-3-azabicyclo[3.1.0]hexane fumarate as colorless crystals, m.p. 153°–155° C.

In the above manner 1-(p-chlorophenyl)-1,2-cyclopropanedicarboximide (U.S. Pat. No. 3,344,026) is converted to N-[4,4-bis(p-fluorophenyl)butyl]-1-(p-chlorophenyl)-1,2-cyclopropanedicarboximide, m.p. 98°–99° C. This compound is reduced as in Example 27 and the base is combined with fumaric acid to give 3-(4,4-bis(p-fluorophenyl)butyl]-1-(p-chlorophenyl)-3-azabicyclo[3.1.0]hexane fumarate as colorless crystals, m.p. 152°–154° C.

EXAMPLE 46

Preparation of
3-[3-(p-Fluorobenzoyl)propyl]-1-phenyl-3-azabicyclo[3.1.0]hexane hydrochloride A mixture of 15.9 g of 1-phenyl-3-azabicyclo[3.1.0]hexane (Example 9), 20.1 g of γ-chloro-p-fluorobutyrophenone and 10 mg of potassium iodide in 100 ml of toluene is refluxed for 24 hours. Filtration gives 11.6 g of 1-phenyl-3-azabicyclo[3.1.0]hexane hydrochloride, m.p. 166°–167° C. Evaporation of the filtrate gives a brown oil which is combined with 2N hydrochloric acid and chloroform. The crystals which form in the chloroform layer are collected by filtration and recrystallized from ethanol to give 3.10 g of 3-[3-(p-fluorobenzoyl)propyl]-1-phenyl-3-azabicyclo[3.1.0]hexane hydrochloride as pale tan crystals, m.p. 151°–153° C.

EXAMPLE 47

Preparation of
1-(m-Methoxyphenyl)-3-azabicyclo[3.1.0]hexane hydrochloride

Methyl-m-methoxymandelate is reacted with phosphorous tribromide by the method of I. P. Beletskaya, Zh. Obshch. Khim., 34, 321 (1964) to give methyl bromo-(m-methoxyphenyl)acetate as a pale yellow liquid, and used below (without further purification).

In a like manner the following mandelate esters can be converted to the corresponding bromoesters:

| Mandelate ester | Bromoester |
| --- | --- |
| ethyl(p-hexyl)mandelate | ethyl bromo-(p-hexylphenyl)-acetate |
| ethyl(p-isopropyl)mandelate | ethyl bromo-(p-cumyl)acetate |
| methyl(m-methyl)mandelate | methyl bromo-(m-tolyl)acetate |
| methyl(o-methyl)mandelate | methyl bromo-(o-tolyl)acetate |

A mixture of 37.0 g of dimethyl 1-(m-methoxyphenyl)-1,2-cyclopropanedicarboxylate (prepared by the method of Example 6 from methyl bromo-(m-methoxyphenyl)acetate and methyl acrylate), 20 g of potassium hydroxide and 200 ml of a 1:1 water-methanol mixture is refluxed 16 hours and the methanol is removed by concentrating. Concentrated hydrochloric acid is added in incremental portions until the pH is one. The mixture is extracted three times with ether, dried and concentrated to give cis-1-(m-methoxyphenyl)-1,2-cyclopropanedicarboxylic acid as a pale yellow gum.

A 34.7 g portion of this diacid, 12 g of urea and 750 ml of xylene is refluxed and stirred for 5 hours. The mixture is cooled, and the supernatant solution is decanted and filtered through magnesium silicate, and the filtrate is concentrated under reduced pressure to give a solid which is recrystallized from ethanol to give 1-(m-methoxyphenyl)-1,2-cyclopropanedicarboximide, m.p. 125°–127° C.

A 3.0 g portion of the above product is mixed with 75 ml of benzene and 20 ml of sodium bis(2-methoxyethoxy)-aluminum hydride (70% benzene solution) is added over a 5 minute period with stirring. After stirring for one-half hour and refluxing for one hour the mixture is cooled and 20 ml of 10N sodium hydroxide is added, followed by saturated sodium chloride. The organic layer is washed with water and then is dried over magnesium sulfate, filtered and evaporated to an oil. The oil is dissolved in ether and hydrogen chloride gas is bubbled in. The solid which forms is recrystallized from acetonitrile to give 1-(m-methoxyphenyl)-3-azabicyclo[3.1.0]hexane hydrochloride as colorless crystals, m.p. 150°–152° C.

EXAMPLE 48

Preparation of
1-(m-Hydroxyphenyl)-3-methyl-3-azabicyclo[3.1.0]hexane hydrochloride 1-(m-Methoxyphenyl)-3-methyl-3-azabicyclo[3.1.0]hexane hydrochloride is combined with sodium hydride and ethanethiol in N,N-dimethylformamide as in Example 40 to give 1-(m-hydroxyphenyl)-3-methyl-3-azabicyclo[3.1.0]hexane hydrochloride.

EXAMPLE 49

Preparation of
1-[(p-Methoxymethyl)phenyl]-3-azabicyclo[3.1.0]hexane hydrochloride A mixture of 2.48 g of cis-dimethyl-1-(p-tolyl)-1,2-cyclopropanedicarboxylate (Example 36) and 1.78 g of N-bromosuccinimide and 5 mg of azabisisobutyronitrile in 50 ml of carbon tetrachloride is irradiated with a 500 watt tungsten lamp for 2 hours. Filtration and evaporation of the filtrate gives cis-dimethyl-1-(α-bromo-p- tolyl)-1,2-cyclopropanedicarboxylate as tan crystals which is used in the subsequent transformation without further purification.

The above benzylic bromide is stirred with a methanolic solution of sodium methoxide for 2 hours and then is refluxed for 3 hours and then the methanol is evaporated. The residue is partitioned between water and dichloromethane and the organic solution is evaporated to give cis-dimethyl-1-[(p-methoxymethyl)phenyl]-1,2-cyclopropanedicarboxylate as a dark oil which is used in the subsequent preparation without further purification.

The preceeding diester is hydrolyzed with ethanolic potassium hydroxide as in Example 6 to give cis-1-[(p-methoxymethyl)phenyl]-1,2-cyclopropanedicarboxylic acid as a brown oil.

The preceeding dicarboxylic acid is refluxed with urea in xylene as in Example 6 to give 1-[(p-methoxymethyl)phenyl]-1,2-cyclopropanedicarboximide as colorless crystals, m.p. 122°–124° C.

The preceeding imide is reduced with borane-tetrahydrofuran as in Example 27 to give 1-[(p-methoxymethyl)phenyl]-3-azabicyclo[3.1.0]hexane hydrochloride.

EXAMPLE 50

Preparation of
3-(n-Hexyl)-1-(p-tolyl)-3-azabicyclo[3.1.0]hexane

The reaction of 1-(p-tolyl)-3-azabicyclo[3.1.0]hexane (Example 36) with sodium borohydride and hexanoic acid, using the reductive alkylation procedure described by G. W. Gribble, et al., Synthesis, 702 (1975), gives 3-(n-hexyl)-1-(p-tolyl)-3-azabicyclo[3.1.0]hexane hydrochloride, m.p. 182°–184° C.

EXAMPLE 51

Preparation of
1-(p-Tolyl)-3-azabicyclo[3.1.0]hexan-2-one

To a slurry of 5.0 g of sodium hydride (50% mineral oil dispersion) in 350 ml of ether, and 0.5 ml of methanol, is added a solution of 24.0 g of methyl bromo-p-tolylacetate, 8.0 g of acrylonitrile and 1.0 ml of methanol at 20°–28° C. over a one-half hour period. After stirring for an additional hour, 10 ml of methanol is added and the ether solution is washed with water. The organic phase is dried over sodium sulfate and and the filtered solution is evaporated to give 5.5 g of yellow crystals, Recrystallization from ethanol gives 3.50 g of cis-2-cyano-1-methoxycarbonyl-1-(p-tolyl)cyclopropane as colorless crystals, m.p. 88°–91° C.

To a solution of 2.15 g of the cyanoester in 100 ml of dry tetrahydrofuran at 0° C. is added 7.5 ml of 1M borane-tetrahydrofuran. This solution is refluxed for thirty minutes and then is held at room temperature for 2 hours. To the cooled solution is added 10 ml of 6N hydrochloric acid, and this solution is warmed on a steam bath for 15 minutes and then is evaporated. The residue is extracted with dichloromethane and evaporation of the solution gives 1-(p-tolyl)-3-azabicyclo[3.1.0]hexan-2-one as a colorless oil, i.r. 5.90 microns.

EXAMPLE 52

Preparation of
2-Methyl-1-(p-tolyl)-3-azabicyclo[3.1.0]hexane hydrochloride

Using the method of M. Takeda, et al., Chem. Pharm. Bull., 24, 2312 (1976), 1-(p-tolyl)-3-azabicyclo[3.1.0]hexan-2-one is reacted with methyllithium followed by sodium borohydride. Excess reagents are decomposed with methanol, followed by 1N hydrochloric acid, and then 1N sodium hydroxide and then evaporation of the solution gives a residue which is dissolved in ether. This solution is dried over sodium sulfate and filtered, and to the filtrate is added dry hydrogen chloride. Filtration of this suspension gives 2-methyl-1-(p-tolyl)-3-azabicyclo[3.1.0]hexane hydrochloride.

EXAMPLE 53

Preparation of
1-(p-Chlorophenyl)-4-ethyl-3-azabicyclo[3.1.0]hexane

To 4.43 g of 1-(p-chlorophenyl)-1,2-cyclopropanedicarboximide in 100 ml of ether is added 16.4 ml of 2M ethylmagnesium bromide. The mixture is allowed to stand at room temperature for 18 hours and then is combined with water. The ether solution is dried over sodium sulfate and evaporated to give 4.05 g of a pink semisolid. Crystallization from ether hexane gives 1-(p-chloropehnyl)-4-ethyl-4-hydroxy-3-azabicyclo[3.1.0]hexan-2-one as colorless crystals, m.p. 154°–157° C.

Evaporation of the mother liquor of the above crystallization gives 1-(p-chlorophenyl)-4-ethyl-4-hydroxy-3-azabicyclo[3.1.0]hexan-2-one as colorless crystals, m.p. 117°–124° C.

Reduction of the hydroxylactams, m.p. 117°–124° C. and 154°–157° C., with sodium borohydride in methanol gives the epimeric 1-(p-chlorophenyl)-4-ethyl-3-azabicyclo[3.1.0]hexanes.

EXAMPLE 54

Preparation of 1-(p-Tolyl)-3-azabicyclo[3.1.0]hexane hydrochloride

A mixture of 3-(p-tolylyl)-3-pyrroline, methylene iodide, and powdered copper in a molar ration of 1:2:4 is heated in benzene for about 50 hours. Filtration and evaporation of the solution gives 1-(p-tolyl)-3-azabicyclo[3.1.0]-hexane.

We claim:

1. An optically active compound of the formula:

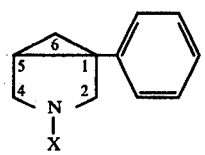

wherein the phenyl moiety is unsubstituted or mono- or di-substituted from the group consisting of halogen, straight chain and mono-branched $C_1$–$C_6$ alkyl, trifluoromethyl, and nitro; X is selected from the group consisting of hydrogen, straight chain $C_1$–$C_8$ alkyl, and a moiety of the formula $C_nH_{2n}R_1$, wherein n is an integer from 1 to 3 and $R_1$ is phenyl; the racemic mixture thereof; the mirror image thereof; and the non-toxic pharmaceutically acceptable salts thereof.

2. An optically active compound according to claim 1, wherein the phenyl moiety is di-substituted from the group consisting of halogen, straight chain $C_1$–$C_6$ alkyl, isopropyl, trifluoromethyl, and nitro; and X is as previously defined.

3. An optically active compound according to claim 1, wherein the phenyl moiety is unsubstituted or mono-substituted from the group consisting of halogen, straight chain $C_1$-$C_6$ alkyl, isopropyl, trifluoromethyl, and nitro; and X is as previously defined.

4. An optically active compound according to claim 3, wherein X is selected from the group consisting of hydrogen and straight chain $C_1$-$C_8$ alkyl.

5. An optically active compound according to claim 4, wherein the phenyl moiety is para or meta substituted from the group consisting of straight chain $C_1$-$C_6$ alkyl, isopropyl, halogen and trifluoromethyl; and X is as previously defined.

6. An optically active compound according to claim 5, wherein the phenyl moiety is para or meta substituted from the group consisting of methyl, ethyl, chloro, fluoro, bromo and trifluoromethyl; and X is as previously defined.

7. An optically active compound according to claim 6, wherein the phenyl moiety is substituted as previously defined; and X is selected from the group consisting of hydrogen and methyl.

8. The compound according to claim 1, 1-(p-Chlorophenyl)-3-azabicyclo[3.1.0]hexane hydrochloride.

9. The compound according to claim 1, (−)-1-(p-Chlorophenyl)-3-azabicyclo[3.1.0]hexane hydrochloride.

10. The compound according to claim 1, (+)-1-(p-Chlorophenyl)-3-azabicyclo[3.1.0]hexane hydrochloride.

11. The compound according to claim 1, 1-Phenyl-3-azabicyclo[3.1.0]hexane hydrochloride.

12. The compound according to claim 1, 3-Methyl-1-phenyl-3-azabicyclo[3.1.0]hexane hydrochloride.

13. The compound according to claim 1, 1-(m-Chlorophenyl)-3-azabicyclo[3.1.0]hexane hydrochloride.

14. The compound according to claim 1, 1-(m-Fluorophenyl)-3-azabicyclo[3.1.0]hexane hydrochloride.

15. The compound according to claim 1, (−)-1-Phenyl-3-azabicyclo[3.1.0]hexane hydrochloride.

16. The compound according to claim 1, (−)-3-Methyl-1-phenyl-3-azabicyclo[3.1.0]hexane hydrochloride.

17. The compound according to claim 1, (−)-1-(p-Chlorophenyl)-3-methyl-3-azabicyclo[3.1.0]hexane hydrochloride.

18. The compound according to claim 1, (+)-1-(p-Chlorophenyl)-3-methyl-3-azabicyclo[3.1.0]hexane hydrochloride.

19. The compound according to claim 1, 1-(p-Chlorophenyl)-3-methyl-3-azabicyclo[3.1.0]hexane hydrochloride.

20. The compound according to claim 1, 3-Benzyl-1-phenyl-3-azabicyclo[3.1.0]hexane hydrochloride.

21. The compound according to claim 1, 3-Phenethyl-1-phenyl-3-azabicyclo[3.1.0]hexane hydrochloride.

22. The compound according to claim 1, 1-(p-Trifluoromethylphenyl)-3-azabicyclo]3.1.0]hexane hydrochloride.

23. The compound according to claim 1, 3-Ethyl-1-phenyl-3-azabicyclo[3.1.0]hexane hydrochloride.

24. The compound according to claim 1, (+)-1-Phenyl-3-azabicyclo[3.1.0]hexane hydrochloride.

25. The compound according to claim 1, 1-(3,4-Dichlorophenyl)-3-azabicyclo[3.1.0]hexane.

26. The compound according to claim 1, (+)-1-Phenyl-3-methyl-3-azabicyclo[3.1.0]hexane hydrochloride.

27. The compound according to claim 1, 1-(4-Chloro-α,α,α-trifluoro-m-tolyl)-3-azabicyclo[3.1.0]hexane hydrochloride.

28. The compound according to claim 1, 1-(p-Nitrophenyl)-3-azabicyclo[3.1.0]hexane hydrochloride.

29. The compound according to claim 1, 1-(p-tolyl)-3-azabicyclo[3.1.0]hexane hydrochloride.

30. The compound according to claim 1, (+)-1-(p-tolyl)-3-azabicyclo[3.1.0]hexane hydrochloride.

31. The compound according to claim 1, (−)-1-(p-tolyl)-3-azabicyclo[3.1.0]hexane hydrochloride.

32. The compound according to claim 1, 3-Methyl-1-(p-tolyl)-3-azabicyclo[3.1.0]hexane hydrochloride.

33. The compound according to claim 1, 1-(p-Chlorophenyl)-3-ethyl-3-azabicyclo[3.1.0]hexane.

34. The compound 3-[4,4-bis(p-Fluorophenyl)butyl]-1-phenyl-3-azabicyclo[3.1.0]hexane Fumarate.

35. The compound 3-[4,4-bis(p-Fluorophenyl)butyl]-1-(p-chlorophenyl)-3-azabicyclo[3.1.0]hexane.

36. The compound according to claim 1, 1-(p-cumyl)-3-azabicyclo[3.1.0]hexane hydrochloride.

37. An optically active compound of the formula:

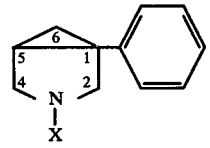

wherein the phenyl moiety is mono- or di-substituted from the group consisting of phenyl, halophenyl and $C_3$-$C_6$ cycloalkyl, X is selected from the group consisting of hydrogen, straight chain $C_1$-$C_8$ alkyl, and a moiety of the formula $C_nH_{2n}R_1$, wherein n is an integer from 1 to 3 and $R_1$ is selected from the group consisting of halophenyl, and bis-halophenyl; the racemic mixture thereof; the mirror image thereof; and the non-toxic pharmaceutically acceptable salts thereof.

38. An optically active compound according to claim 37, wherein the phenyl moiety is di-substituted from the group consisting of phenyl, halophenyl and $C_3$-$C_6$ cycloalkyl; and X is as previously defined.

39. An optically active compound according to claim 37, wherein the phenyl moiety is mono-substituted from the group consisting of phenyl, halophenyl and $C_3$-$C_6$ cycloalkyl; and X is as previously defined.

40. An optically active compound according to claim 39, wherein X is selected from the group consisting of hydrogen and straight chain $C_1$-$C_8$ alkyl.

41. An optically active compound according to claim 40, wherein the phenyl moiety is para or meta substituted from the group consisting of phenyl, and halophenyl; and X is as previously defined.

42. An optically active compound according to claim 41, wherein the phenyl moiety is para or meta substituted from the group consisting of phenyl, monochlorophenyl, and di-chlorophenyl; and X is as previously defined.

43. An optically active compound according to claim 42, wherein the phenyl moiety is substituted as previously defined; and X is selected from the group consisting of hydrogen and methyl.

44. The compound according to claim 37, 1-(4-biphenyl)-3-azabicyclo[3.1.0]hexane.

45. The compound according to claim 37, 1-(p-cyclohexylphenyl)-3-azabicyclo[3.1.0]hexane.

46. An optically active compound of the formula:

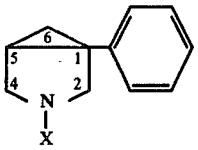

wherein the phenyl moiety is unsubstituted or mono- or di-substituted from the group consisting of halogen, straight chain $C_1$–$C_6$ alkyl, trifluoromethyl, and nitro; X is selected from the group consisting of $C_3$–$C_6$ cycloalkylmethyl, $C_3$–$C_6$ alkenyl and $C_3$–$C_6$ alkynyl; the racemic mixture thereof; the mirror image thereof; and the non-toxic pharmaceutically acceptable salts thereof.

47. An optically active compound according to claim 46, wherein the phenyl moiety is di-substituted from the group consisting of halogen, straight chain $C_1$–$C_6$ alkyl, trifluoromethyl, and nitro; and X is as previously defined.

48. An optically active compound according to claim 46, wherein the phenyl moiety is unsubstituted or mono-substituted from the group consisting of halogen, straight chain $C_1$–$C_6$ alkyl trifluoromethyl, and nitro; and X is as previously defined.

49. An optically active compound according to claim 48, wherein X is selected from the group consisting of cyclopropylmethyl, cyclobutylmethyl, cyclopentylmethyl, allyl, butenyl, dimethylallyl and propargyl.

50. An optically active compound according to claim 49, wherein the phenyl moiety is para or meta substituted from the group consisting of straight chain $C_1$–$C_6$ alkyl, halogen and trifluoromethyl; and X is as previously defined.

51. An optically active compound according to claim 50, wherein the phenyl moiety is para or meta substituted from the group consisting of methyl, ethyl, chloro, fluoro, bromo and trifluoromethyl; and X is as previously defined.

52. An optically active compound according to claim 51, wherein the phenyl moiety is substituted as previously defined; and X is selected from the group consisting of cyclopropylmethyl, allyl and propargyl.

53. An optically active compound of the formula:

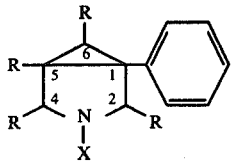

wherein the phenyl moiety is unsubstituted or mono- or di-substituted from the group consisting of halogen, straight chain $C_1$–$C_6$ alkyl, trifluoromethyl, and nitro; X is selected from the group consisting of hydrogen, straight chain $C_1$–$C_8$ alkyl, and a moiety of the formula $C_nH_{2n}R_1$, wherein n is an integer from 1 to 3 and $R_1$ is phenyl; R is selected from the group consisting of hydrogen and $C_1$–$C_3$ alkyl; with the proviso that at least one R must be selected from the group consisting of $C_1$–$C_3$ alkyl; the racemic mixture thereof; the mirror image thereof; and the non-toxic pharmaceutically acceptable salts thereof.

54. An optically active compound according to claim 53, wherein the phenyl moiety is di-substituted from the group consisting of halogen, straight chain $C_1$–$C_6$ alkyl, trifluoromethyl, and nitro; and R and X are as previously defined.

55. An optically active compound according to claim 53, wherein the phenyl moiety is unsubstituted or mono-substituted from the group consisting of halogen, straight chain $C_1$–$C_6$ alkyl, trifluoromethyl, and nitro; and R and X are as previously defined.

56. An optically active compound according to claim 55, wherein X is selected from the group consisting of hydrogen and straight chain $C_1$–$C_8$ alkyl; and R is as previously defined.

57. An optically active compound according to claim 56, wherein the phenyl moiety is para or meta substituted from the group consisting of straight chain $C_1$–$C_6$ alkyl, halogen and trifluoromethyl; and R and X are as previously defined.

58. An optically active compound according to claim 57, wherein the phenyl moiety is para or meta substituted from the group consisting of methyl, ethyl, chloro, fluoro, bromo and trifluoromethyl; X is as previously defined; and R is mono-substituted at the carbon 2- or carbon 4-position.

59. An optically active compound according to claim 58, wherein the phenyl moiety is substituted as previously defined; X is selected from the group consisting of hydrogen and methyl; and R is as previously defined.

60. The compound according to claim 53, 2,3-dimethyl-1-(p-tolyl)-3-azabicyclo[3.1.0]hexane.

61. The compound according to claim 53, 3,4-dimethyl-1-(p-tolyl)-3-azabicyclo[3.1.0]hexane.

62. The compound according to claim 53, 2-methyl-1-(p-tolyl)-3-azabicyclo[3.1.0]hexane.

63. The compound according to claim 53, 4-methyl-1-(p-tolyl)-3-azabicyclo[3.1.0]hexane.

64. The compound according to claim 1, 1-(p-ethylphenyl)-3-azabicyclo[3.1.0]hexane hydrochloride.

65. The compound according to claim 1, 1-(p-hexylphenyl)-3-azabicyclo[3.1.0]hexane hydrochloride.

66. The compound according to claim 1, 1-(m-tolyl)-3-azabicyclo[3.1.0]hexane hydrochloride.

67. The compound according to claim 1, 1-(p-bromophenyl)-3-azabicyclo[3.1.0]hexane hydrochloride.

68. The compound according to claim 1, 1-(p-fluorophenyl)-3-azabicyclo[3.1.0]hexane hydrochloride.

69. The compound according to claim 1, 1-($\alpha,\alpha,\alpha$-trifluoro-m-tolyl)-3-azabicyclo[3.1.0]hexane hydrochloride.

* * * * *